US006165484A

United States Patent [19]
Raad et al.

[11] Patent Number: 6,165,484
[45] Date of Patent: *Dec. 26, 2000

[54] EDTA AND OTHER CHELATORS WITH OR WITHOUT ANTIFUNGAL ANTIMICROBIAL AGENTS FOR THE PREVENTION AND TREATMENT OF FUNGAL INFECTIONS

[75] Inventors: Issam Raad, Houston, Tex.; Robert Sheretz, Winston-Salem, N.C.; Ray Hachem, Houston, Tex.

[73] Assignees: Wake Forest University, Winston Salem, N.C.; Board of Regents, The University of Texas Sysytem, Austin, Tex.

[*] Notice: This patent is subject to a terminal disclaimer.

[21] Appl. No.: 09/139,522

[22] Filed: Aug. 25, 1998

Related U.S. Application Data

[60] Provisional application No. 60/056,970, Aug. 26, 1997.

[51] Int. Cl.[7] .............................. A01N 25/00; A61K 31/70
[52] U.S. Cl. .............................................. 424/405; 514/31
[58] Field of Search ................................ 424/405; 514/31

[56] References Cited

U.S. PATENT DOCUMENTS

| | | |
|---|---|---|
| 4,054,139 | 10/1977 | Crossley . |
| 4,107,121 | 8/1978 | Stoy . |
| 4,411,648 | 10/1983 | Davis et al. . |
| 4,442,133 | 4/1984 | Greco et al. . |
| 4,569,673 | 2/1986 | Tesi . |
| 4,678,660 | 7/1987 | McGary et al. . |
| 4,749,585 | 6/1988 | Greco et al. . |
| 4,764,164 | 8/1988 | Sasaki . |
| 4,776,334 | 10/1988 | Prionas . |
| 4,847,049 | 7/1989 | Yamamoto . |
| 4,886,505 | 12/1989 | Haynes et al. . |
| 4,895,566 | 1/1990 | Lee . |
| 4,906,238 | 3/1990 | Greenfield et al. . |
| 4,917,686 | 4/1990 | Bayston et al. . |
| 4,952,419 | 8/1990 | De Leon et al. . |
| 4,973,320 | 11/1990 | Brenner et al. . |
| 5,002,792 | 3/1991 | Vegoe . |
| 5,013,306 | 5/1991 | Solomon et al. . |
| 5,037,380 | 8/1991 | Jacobsen et al. . |
| 5,071,407 | 12/1991 | Termin et al. . |
| 5,087,240 | 2/1992 | Sibalis . |
| 5,143,071 | 9/1992 | Keusch et al. . |
| 5,147,291 | 9/1992 | Cukier . |
| 5,202,449 | 4/1993 | Hasagawa . |
| 5,217,493 | 6/1993 | Raad et al. . |
| 5,324,275 | 6/1994 | Raad et al. . |
| 5,362,754 | 11/1994 | Raad et al. . |
| 5,542,935 | 8/1996 | Unger et al. ............................ 424/450 |
| 5,688,516 | 11/1997 | Raad et al. . |

FOREIGN PATENT DOCUMENTS

94/10838   5/1994   WIPO .

OTHER PUBLICATIONS

Tanaka, *Chemical Abstracts*, vol. 116, #102221, 1992.
Rodwell et al., *Chemical Abstracts*, vol. 112, #213574, 1990.
Adair et al., "Resistance of Pseudomonas to quaternary ammonium compounds," *Applied Microbiology*, 21(6):1058–1063, 1971.
AHFS Drug Information, McEvoy et al., editors, "Minocycline–HC1," pp. 318–319 and "Edetate Disodium," pp. 1805–1807, 1992.
Anwar et al., "Interaction of biofilm bacteria with antibiotics in a novel in vitro chemostat system," *Antimicrobial Agents and Chemotherapy*, 33(10):1824–1826, 1989.
Anwar et al., "Tobramycin resistance of mucoid *pseudomonas aeruginosa* biofilm grown under iron limitation," *Journal of Antimicrobial Chemotherapy*, 24:647–655, 1989.
Beaumont, "In–vivo experiments with ethylenediamine–tetra–acetic acid and investigations into its action of penicillin–resistant *Staphylococcus aureus*," *The Medical Journal of Australia*, pp. 1017–1020, 1970.
Benisek and Richards, "Attachment of metal–chelating functional groups to hen eggs white lysozyme," *J. Biol. Chem.*, 243(16):4267–4271, 1968.
Berger et al., "Electrically generated silver ions: quantitative effects on bacterial and mammalian cells," *Antimicrobial Agents and Chemotherapy*, 9:357–358, 1976.
Brown and Foster, "Effect of slime on the sensitivity of *Pseudomonas aeruginosa* to EDTA and polymyxin," *Journal of Pharmacy and Pharmacology (Abstract)*, British Pharmaceutical Conference, 108th Meeting, Glasgow, 23(Suppl.):236S, Sep. 13–17, 1971.
Brown, "Effects of the microbial environment on drug resistance," *J. Sci. Fd Agric.*, 25:227–230, 1974.
Campbell, In: *Monoclonal Antibody Technology, Laboratory Techniques in Biochemistry and Molecular Biology*, vol. 13, Burden and Von Knippenberg, (Eds.), Amsterdam, Elseview, Chapter 3, pp. 75–83, 1984.
Clumeck et al., "Treatment of severe staphylococcal infections with a rifampicin–minocycline association," *Journal of Antimicrobial Chemotherapy*, 13(Suppl. C):17–22, 1984.
Condamine et al., "Acquired sideroblastic anaemia during treatment of Wilson's disease with triethylene tetramine dihydrochloride," *British Journal of Haematology*, 83:166–168, 1993.
Crosby and Gump, "Activity of cefoperazone and two b–lactamase inhibitors, sulbactam and clavulanic acid, against *bacteroides* spp. correlated with b–lactamase production," *Antimicrobial Agents and Chemotherapy*, 22(3):398–405, 1982.
Dankert and Schut, "The antibacterial activity of chloroxylenol in combination with ethylenediaminetetra–acetic acid," *Journal of Hygiene*, 76(1):11–22, 1976.

(List continued on next page.)

*Primary Examiner*—Kevin E. Weddington
*Attorney, Agent, or Firm*—Fulbright & Jaworski

[57] ABSTRACT

A pharmaceutical composition comprising at least one antifungal agent and at least one chelator, and a method for administering the pharmaceutical composition to a patient having a fungal infection. Another aspect provides a pharmaceutical composition comprising at least one chelator, at least one antifungal agent and at least one monoclonal antibody, wherein the monoclonal antibody is operatively attached to the chelator, and a method of administering this composition to a patient having a fungal infection.

10 Claims, 11 Drawing Sheets

OTHER PUBLICATIONS

Davis and Iannetta, "Influence of serum and calcium on the bactericidal activity of gentamicin and carbenicillin on *Pseudomonas aeruginosa*," *Applied Microbiology*, 23(4):775–779, 1972.

Delmotte et al., "Study of the sensitivity of pyocyanic bacillus (*Pseudomonas aeruginosa*) to antiseptics and antibiotics. IV. Synergism or antagonism between antiseptics [French]," *Therapie*, 27(3):445–455, 1972.

DeRiemer et al., "BLEDTA: Tumor localization by a bleomycin analogue containing a metal–chelating group," *J. Med. Chem.*, 22:1019–1023, 1979.

Dialog Search Report printed in USA in 1992.

Dickinson and Lewandowski, "Manganese bifouling and the corrosion behavior of stainless steel," *Biofouling* 10(1–3);79–93, 1996.

Diver et al., "The accumulation of five quinolone antibacterial agents by *Escherichia coli*," *Journal of Antimicrobial Chemotherapy*, 25:319–333, 1990.

Doss et al., "Effect of EDTA on bacterial resistance to antibiotics, a bacteriological and clinical study," *Journal of the Egyptian Medical Association*, 52(11):929–941, 1969.

Evans and Holmes, "Effect of vancomycin hydrochloride on *staphylococcus epidermidis* biofilm associated with silicon elastomer," *Antimicrobial Agents and Chemotherapy*, 31(6):889–894, 1987.

Farber et al., "*Staphylococcus epidermidis* extracted slime inhibits the antimicrobial action of glycopeptide antibiotics," *Journal of Infectious Diseases*, 161:37–40, 1990.

Farca et al., "Potentiation of the in vitro activity of some antimicrobial agents against selected gram–negative bacteria by EDTA–tromethamine," *Veterinary Research Communications*, 17(2):77–84, 1993.

Flowers et al., "Efficacy of an attachable subcutaneous cuff for the prevention of intravascular catheter–related infection," *Journal of the American Medical Association*, 261:878–883, 1988.

Fuursted, "Synergism and mechanism of subinhibitory concentration of streptomycin on *Streptococcus faecalis*," *APMIS*, 97:27–32, 1989.

Gefter et al., "A simple method for polyethylene glycol–promoted hybridization of mouse myeloma cells," *Somatic Cell Genet.*, 3:231–236, 1977.

Gelewitz et al., "Some quantitative aspects of the reaction of diazonium compounds with serum albumin," *Arch. Biochem. Biophys.*, 53:411–424, 1954.

Gerberick and Castric, "In Vitro Susceptibility of *Pseudomonas aeruginosa* to Carbenicillin, Glycine, and Ethylenediaminetetraacetic Acid Combinations," *Antimicrobial Agents and Chemotherapy*, 17(4):732–735, 1980.

Goding, 1986, In: *Monoclonal Antibodies: Principles and Practice*, 2nd ed., Academic Press, Orlando, FL, pp. 60–74, 1986.

*Goodman and Gilman's The Pharmacological Basis of Therapeutics*, Eighth Edition, Pergamon Press, Chapter 48, "Antimicrobial Agents," pp. 1117–1125, 1607–1608, 1990.

Goodwin et al., "[111]In–labeled radiopharmaceuticals and their clinical use," In: *Radiopharmaceuticals*, Society of Nuclear Medicine, New York, p. 80–101, 1975.

Gu and Neu, "In vitro activity of dactimicin, a movel pseudodisaccharide aminoglycoside, compared with activities of other aminoglycosides," *Antimicrobial Agents and Chemotherapy*, 33(11):1998–2003, 1989.

Harper and Epis, "effect of chlorhexidine/edta/tris against bacterial isolates from clinical specimens," *Microbios*, 51:107–112, 1987.

Henrickson and Dunne, Jr., "Modification of central venous catheter flush solution improves in vitro antimicrobial activity," *The Journal of Infectious Diseases*, 166:944–946, 1992.

Hnatowich et al., "Radioactive labeling of antibody: a simple and efficient method," *Science*, 220:613–615, 1983.

Houlsby et al., "Effects of preservatives, steroids, and ethylenediaminetetraacetate on the antimicrobial activity of sulfacetamide," *Journal of Pharmaceutical Sciences*, 72(12):1401–1403, 1983.

Hoyle et al., "The biofilm glycocalyx as a resistance factor," *Journal of Antimicrobial Chemotherapy*, 26:1–6, 1990.

Inman et al., "Determination of EDTA in vancomycin by liquid chromatography with absorbance ratioing for peak identification," *Journal of Pharmaceutical & Biomedical Analysis*, 8(6):513–520, 1990.

Kamal et al., "Reduced intravascular catheter infection by antibiotic bonding", *JAMA*, 265(18):2364–2368, 1991.

Khaw et al., "Myocardial infarct imaging of antibodies to caninie cardiac myosin with indium–111–diethylenetriamine pentaacetic acid," *Science*, 209:295–297, 1980.

Khoury and Costerton, "Bacterial biofilms in nature and disease," *Dialogues in Pediatric Urology*, 14(10):2–5, 1991.

Knasmüller et al., "Investigations on the use of EDTA–permeabilized *E. coli* cells in liquid suspension and animal––mediated genotoxicity assays," *Mutation Research*, 216:189–196, 1989.

Köhler and Milstein, "Continuous cultures of fused cells secreting antibody of predefined specificity," *Nature*, 256:495–497, 1975.

Kosmider et al., "Antibacterial action of complexing compounds. The influence of disodium versenate on microorganisms in vitro," *Archivum Immunologiae et Therapiae Experimentalis*, 20(6):931–937, 1972.

Krejcarek and Tucker, "Covalent attachment of chelating groups to macromolecules," *Biochem. Biophys. Res. Commun.*, 77:581–585, 1977.

Kropec et al., "In vitro activity of sodium bisulfite and heparin against Staphylococci: new strategies in the treatment of catheter–related infection," *The Journal or Infectious Diseases*, 168:235–7, 1993.

Leung et al., "The attachment of metal–chelating groups to proteins: tagging of albumin by diazonium coupling and use of the products as radiopharmaceuticals," *Int. J. Appl. Radiot. Isot.*, 29:687–692, 1978.

Light and Riggs, Jr., "Effect of triethylenetetramine dihydrochloride on the antibiotic susceptibility of *Pseudomonas aeruginosa*," *Antimicrobial Agents and Chemotherapy*, 13(6):979–984, 1978.

Machnicka et al., "Influence of 0.02 M EDTA and 3 M KCl on surface of *hymenolepis diminuta* and composition of isolated proteins," *Folia Histochemica Et Cytobiologica*, 24(1):65–70, 1986.

Maki et al., "An attachable silver–impregnated cuff for prevention of infection with central venous catheter: a prospective randomized multicenter trail," *The American Journal of Medicine*, 85:307–314, 1988.

Maki et al., VitaCuff®, Vitaphore Corp., Menol Park, California.

Marino et al., "Electrochemical properties of silver–nylon fabrics," *Journal of the Elecrochemical Society*, 68–72, 1985.

Marshall, Kevin C., "Biofilms: an overview of bacterial adhesion, activity, and control at surfaces," *ASM News*, 58(4):202–207, 1992.

McMurry et al., "Susceptible *Escherichia coli* cells can actively excrete tetracyclines," *Antimicrobial Agents and Chemotherapy*, 24(4):544–551, 1983.

Meares et al., "Covalent attachment of metal chelates to proteins: The stability in vivo and in vitro of the conjugate of albumin with a chelate of $^{111}$indium," *Proc. Natl. Acad. Sci. U.S.A.*, 73:3803–3806, 1976.

Meares and Wensel, "Metal chelates as probes of biological systems," *Acc. Chem. Res.*, 17:202–209, 1984.

Mermel et al., "Surface antimicrobial activity of heparin-–bonded and antiseptic–impregnated vascular catheters," *The Journal of Infectious Diseases*, 167:920–4, 1993.

Miyake et al., "Effects of ethylenediaminetetraacetic acid and gentamicin on the antibacterial activity of pyridone carboxylic acid derivatives against Gram–negative bacilli," *Journal of Antimicrobial Chemotherapy*, 17:327–332, 1986.

Nezval and Ritzerfeld, "Antibacterial effect of the combination rifampicin–EDTA on Pseudomonas and Proteus," *Archiv fur Hygiene und Bakteriologie*, 153(6):548–551, 1969.

Nickel et al., "Tobramycin resistance of *pseudomonas aeruginosa* cells growing as a biofilm on urinary catheter material," *Antimicrobial Agents and Chemotherapy*, 27(4):619–624, 1985.

Nickel, J. Curtis, "Bacterial biofilms in urological infectious diseases," *Dialogues in Pediatric Urology*, 14(10):7–8, 1991.

Nielsen and Close, "Edetate disodium–mediated chloramphenicol resistance in *Pseudomonas cepacia*," *Journal of Pharmaceutical Sciences*, 71(7):833–834, 1982.

Nowakowska et al., "EDTA disodium salt as an agent modifying penicillin sensitivity of *Staphylococcus–aureus* 1. Effect In–Vitro on Penicillin Resistant *Staphylococcus–Aureus*," *Med. Dosw. Mikrobiol.*, 34(1–2):7–12, 1982 (Abstract).

Raad et al., "Infectious complications of indwelling vascular catheters," *Clinical Infectious Diseases*, 15:197–210, 1992.

Raad et al., "Quantitative tip culture methods and the diagnosis of central venous catheter–related infections," *Diagn. Microbiol. Infect. Dis.*, 15:13–20, 1992.

Rawal and Owen, "Combined action of sulfamethoxazole, trimethoprim, and ethylenediaminetetraacetic acid on *Pseudomonas aeruginosa*," *Applied Microbiology*, 21(2):367–368, 1971.

Reid and Speyer, "Rifampicin inhibition of ribonucleic acid and protein synthesis in normal ethylenediaminetetraacetic acid–treated *Escherichia coli*," *Journal of Bacteriology*, 104(1):376–389, 1970.

Reid, Gregor, "Important components in the adhesion of bacteria to prosthetic devices," *Dialogues in Pediatric Urology*, 14(10):6–7, 1991.

*Remington's Pharmaceutical Sciences*, 18th Edition, Alfonso R. Gennaro, Editor, Mack Publishing Company, Easton, PA, "Minocycline HCl," p. 1213, 1990.

Richards, "Inactivation of resistant *Pseudomonas aeruginosa* by antimicrobial combinations," *J. Pharm. Pharmac.*, 23(Suppl.):136S–140S, 1971.

Root et al., "Inhibitory effect of disodium EDTA upon the growth of *staphylococcus epidermidis* in vitro: relation to infection prophylaxis of hickman catheters," *Antimicrobial Agents and Chemotherapy*, 32(11):1627–1631, 1988.

Rosen and Klebanoff, "Role of iron and ethylenediaminetetraacetic acid in the bactericidal activity of a superoxide anion–generating system," *Archives of Biochemistry and Biophysics*, 208(2):512–519, 1981.

Rudy et al., "Action in vitro of disodium ethylenediaminetetraacetic acid (Na2EDTA) and antibiotics on resistant strains of *Staphylococcus aureus* [Polish]," *Med. Dosw. Mikrobiol.*, 45(2):153–158, 1993.

Rudy et al., "Effects of disodium salt of ethylenediaminetetraacetic acid (Na2EDTA) and tetracyclines on drug resistant bacteria. Studies in vitro [Polish]," *Med. Dosw. Mikrobiol.*, 43(3–4):127–134, 1991.

Said et al., "Expression of H 1 outer–membrane protein of *Pseudomonas aeruginosa* in relation to sensitivity to EDTA and polymyxin B," *Journal of Medical Microbiology*, 24:267–274, 1987.

Seeger and Hentschel, "The influence of Ethylenediaminetetraacetic acid (EDTA) on the antibacterial activity of some antibiotics and their enteral adsorption in the pig," *Arzneim.–Forsch.*, 10:1590–1594, 1971.

Segreti et al., "In vitro activity of minocycline and rifampin against Staphylococci," *Diagn. Microbiol. Infect. Dis.*, 12:253–255, 1989.

Sherertz et al., "Efficacy of antibiotic–coated catheters in preventing subcutaneous *Staphylococcus aureus* infection in rabbits," *J. Infect. Dis.*, 167:98–106, 1993.

Sherertz et al., "Three–year experience with sonicated vascular catheter cultures in a clinical microbiology laboratory," *J. Clin. Microbiol.*, 28(1):76–82, 1990.

Sokolovsky et al., "Conversion of 3–nitrotyrosine to 3–aminotyrosine in peptides and proteins," *Biochem. Biophsy. Res. Commun.*, 27(1):20–25, 1967.

Solomon, Donald D., "Antibiotic releasing polymers," *Journal of Controlled Release*, 6:343–352, 1987.

Spadaro et al., "Antibacterial effects of silver electrodes with weak direct current," *Antimicrobial Agents and Chemotherapy*, 6:637–642, 1974.

Sundberg et al., "Selective binding of metal ions to macromolecules using bifunctional analogs of EDTA," *J. Med. Chem.*, 17:1304–1307, 1974.

*The Merck Index: An Encyclopedia of Chemicals, Drugs, and Biologicals*, Eleventh Edition, Susan Budavari, Editor, Merck & Co., Inc., Publishers, Rahway, NJ, "Minocycline," p. 976, 1989.

Tojo et al., "Isolation and characterization of a capsular polysaccharide adhesin from *Staphylococcus epidermisis*," *J. of Infect. Dis.*, 157(4):713–722, 1988.

Vergeres and Blaser, "Amikacin, ceftazidime, and flucloxacillin against suspended and adherent *Pseudomonas aeruginosa* and *Staphylococcus epidermidis* in an in vitro model of infection," *J. of Infect. Dis.*, 165:281–289, 1992.

Weiser, "Combinations of edetic acid and antibiotics in the treatment of rat burns infected with a resistant strain of *Pseudomonas aeruginosa*," *The Journal of Infectious Diseases*, 128(4):566–569, 1973.

Winstanley and Hastings, "Synergy between penicillin and gentamicin against enterococci," *Journal of Antimicrobial Chemotherapy*, 25:551–560, 1990.

Yamada et al., "Susceptibility of micro–organisms to active oxygen species: sensitivity to the xanthine–oxidase–mediated antimicrobial system," *Journal of General Microbiology*, 133:2007–2014, 1987.

Yeh et al., "Decomposition rates of radiopharmaceutical indium chelates in serum," *J. Radioanal. Chem.*, 53:327–336, 1979.

Yeh et al., et al., "A new route to "bifunctional" chelating agents: conversion of amino adds to analogs of ethylene-dinitrilotetraacetic acid," *Anal. Biochem.,* 100:152–159, 1979.

Yourassowsky et al., "Combination of minocycline and rifampicin against methicillin– and gentamicin–resistant *Staphylococcus aureus,*" *J. Clin. Pathol.,* 34:559–563, 1981.

Yuk et al., "Minocycline as an alternative antistaphylococcal agent," *Review of Infectious Diseases,* 13:1023–1024, 1991.

Zaremba et al., "EDTA disodium salt as a factor modifying *Staphylococcus aureus* sensitivity to penicillin. II. Effect on *Staphylococcus aureus* in its various growth phases. [Polish]," *Med. Dosw. Mikrobiol.,* 34(1–2):17–26, 1982.

Zhang and Dexter, "Effect of biofilms on crevice corrosion of stainless steels in coastal seawater," *Corrosion,* 51(1):56–66, 1995.

Zietkiewicz et al., "Effect of EDTA combined with gentamicin on bacterial flora of burn wounds. [Polish]," *Polski Tygodnik Lekarski.,* 40(32):904–906, 1985.

Zinner et al., "Antistaphylococcal activity of rifampin with other antibiotics," *J. of Infect. Dis.,* 144(4):365–371, 1981.

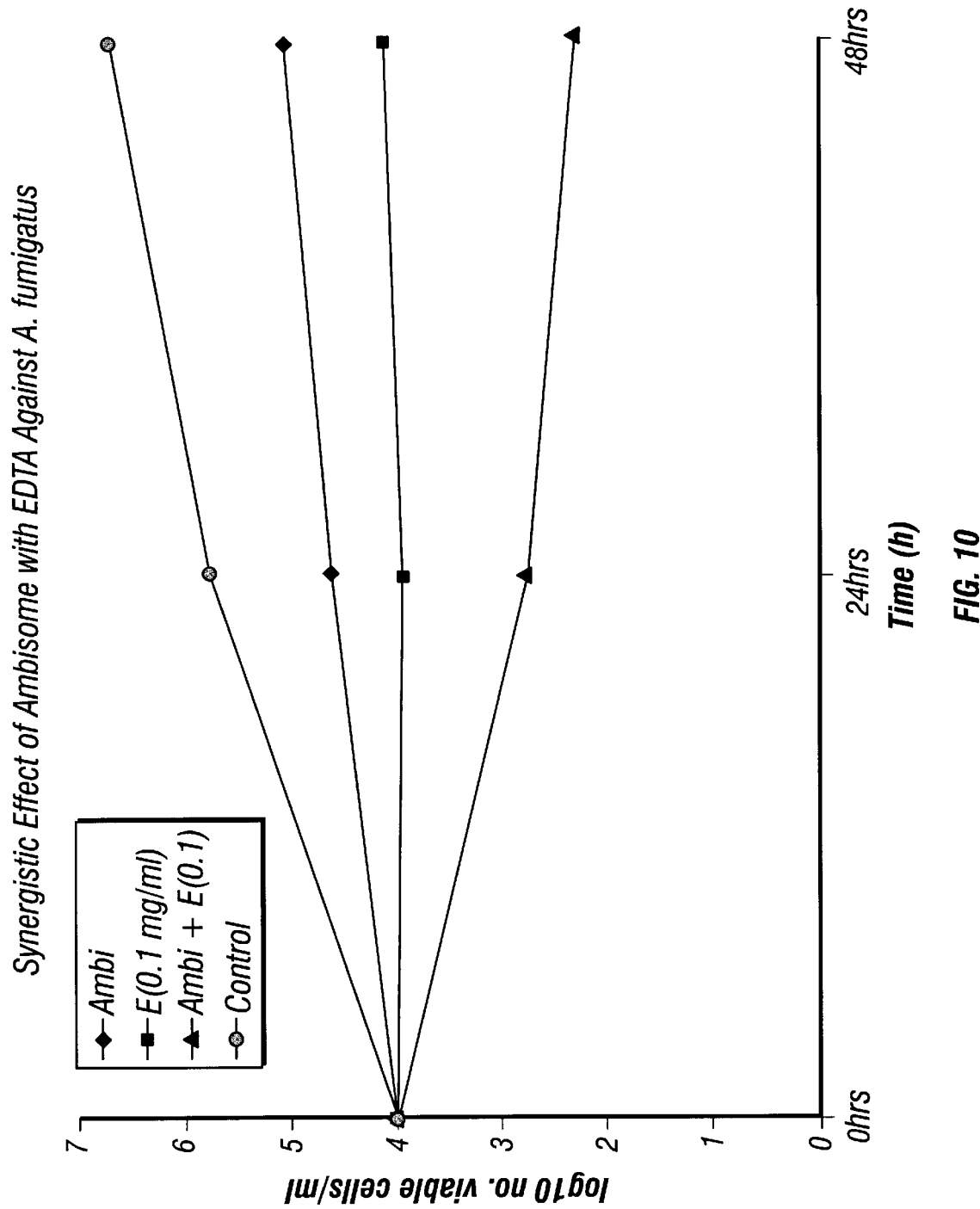

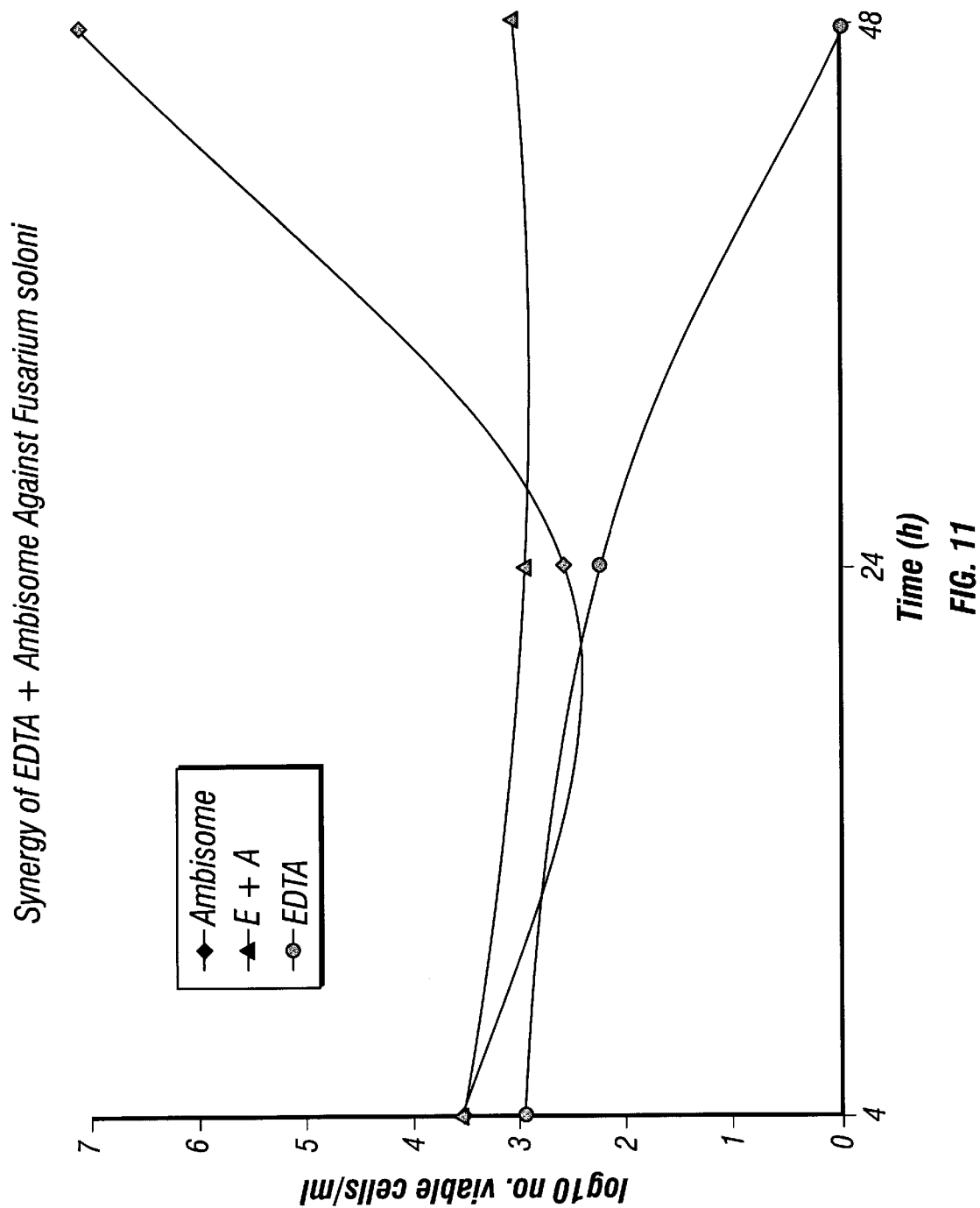

EDTA AND OTHER CHELATORS WITH OR WITHOUT ANTIFUNGAL ANTIMICROBIAL AGENTS FOR THE PREVENTION AND TREATMENT OF FUNGAL INFECTIONS

This application claims the benefit of U.S. Provisional Application No. 60/056,970, filed Aug. 26, 1997.

BACKGROUND OF THE INVENTION

1. Field of the Invention

The present invention relates generally to the treatment of fungal infections in mammals. More particularly, the present invention provides methods of treating fungal infections in mammals using pharmaceutical preparations including chelator(s), antifungal agents, and/or monoclonal antibodies. The invention further provides pharmaceutical compositions useful for treating fungal infections.

2. Description of Related Art

Fungi, particularly species of Candida, Aspergillus, and Fusarium are a major cause of infection-related mortality in patients with leukemia and lymphoma. In addition, fungal infection is a major cause of mortality in patients with congenital and acquired deficiencies of the immune system.

For example, several species of Aspergillus are known to cause invasive sinopulmonary infections in seriously immunocompromised patients. Following inhalation of spores, clinical aspergillosis can occur in three major presentations. The first presentation, allergic bronchopulmonary aspergillosis, develops when Aspergillus species colonize the bronchial tree and release antigens that cause a hypersensitivity pneumonitis. The second presentation, aspergilloma or "fungus ball," develops in pulmonary cavities, often in concert with other lung diseases such as tuberculosis. The third form, invasive pulmonary or disseminated aspergillosis, is a life threatening infection with a high mortality rate.

The drug of choice in treatment of invasive aspergillosis, as well as in most other systemic mycoses, is Amphotericin B. Amphotericin B is a polyene antibiotic produced from a strain of *Streptomyces nodosus*. It is a lipophilic compound which binds to ergosterols in fungal membranes, resulting in the formation of transmembrane channels which allow the escape of metabolites essential to maintaining the viability of the fungal cell. Mammalian cell membranes also contain sterols, and it is believed that this same mechanism of action is responsible for the damaging effects which Amphotericin B is known to exert on mammalian kidney, hematopoietic and central nervous system tissues.

Amphotericin B is not soluble in aqueous solution, and for this reason it is supplied commercially in the form of a colloidal suspension comprising Amphotericin B, desoxycholate, and buffers suspended in a glucose solution. This suspension is usually administered to the patient intravenously over a period of from two to six hours; faster infusions can result in cardiorespiratory arrest. Other possible untoward effects of administering Amphotericin B include fever, nausea and vomiting, diarrhea, renal dysfunction, anemia, hypotension, headache, vertigo, and loss of hearing. Amphotericin B is also available in the form of a phospholipid complex (ABELCET®, e.g.), which offers the advantage of somewhat reduced toxicity for those patients who do not tolerate free Amphotericin B well, although many of the same untoward side effects may be observed in patients receiving this lipid complex form of the drug.

As a consequence of the potential seriousness of its toxic side effects, there is a clear need for an alternative to treating systemic mycoses solely with Amphotericin B and/or other harsh antifungal agents.

SUMMARY OF THE INVENTION

The present invention provides an effective method of treating a systemic fungal infection comprising the steps of obtaining a therapeutically effective amount of a pharmaceutical composition comprising at least one chelator, at least one antifungal agent and a pharmaceutical excipient, diluent or adjuvant, and administering said pharmaceutical composition to a patient having a fungal infection.

For the purposes of this disclosure, the phrase "therapeutically effective amount" is defined as a dosage sufficient to induce a fungicidal or fungistatic effect upon fungi contacted by the composition. That amount of the pharmaceutical composition which is therapeutically effective will depend upon the ingredients comprising the composition, as well as the treatment goals.

For the purposes of this disclosure, the phrase "a chelator" denotes one or more chelators. As used herein, the term "chelator" is defined as a molecule comprising nonmetal atoms, two or more of which atoms are capable of linking or binding with a metal ion to form a heterocyclic ring including the metal ion.

For the purposes of this disclosure, the phrase "an antifungal agent" denotes one or more antifungal agents. As used herein, the term "antifungal agent" is defined as a compound having either a fungicidal or fungistatic effect upon fungi contacted by the compound.

As used herein, the term "fungicidal" is defined to mean having a destructive killing action upon fungi. As used herein, the term "fungistatic" is defined to mean having an inhibiting action upon the growth of fungi.

As used herein the terms "contact", "contacted", and "contacting", are used to describe the process by which a pharmacological agent, e.g., any of the compositions disclosed in the present invention, comes in direct juxtaposition with the target cell.

Preferable chelators for use in the present invention include, but are not limited to, ethylenediamine-N,N,N',N'-tetraacetic acid (EDTA); the disodium, trisodium, tetrasodium, dipotassium, tripotassium, dilithium and diammonium salts of EDTA; the barium, calcium, cobalt, copper, dysprosium, europium, iron, indium, lanthanum, magnesium, manganese, nickel, samarium, strontium, and zinc chelates of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid) hemihydrate; N-(2-hydroxyethyl)ethylenediamine-N,N',N'-triacetic acid; ethylenediamine-N,N,N',N'-tetrakis (methylenephosponic acid); O,O'-bis(2-aminoethyl) ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris (methylenephosphoric acid); 7,19,30-trioxa-1,4,10,13,16, 22,27,33-octaazabicyclo[11,11,11] pentatriacontane hexahydrobromide; and triethylenetetramine-N,N,N',N", N''',N''''-hexaacetic acid. It is contemplated that any chelator which binds barium, calcium, cerium, cobalt, copper, iron, magnesium, manganese, nickel, strontium, or zinc will be acceptable for use in the present invention.

More preferably, the chelators for use in conjunction with the present invention may include ethylenediamine-N,N,N',N'-tetraacetic acid (EDTA); the disodium, trisodium, tetrasodium, dipotassium, tripotassium, dilithium and diammonium salts of EDTA; 1,3-diamino-2-hydroxypropane-N,N,N',N'-tetraacetic acid; 1,3-diaminopropane-N,N,N',N'-tetraacetic acid; O,O'-bis(2-aminoethyl)ethyleneglycol-N,N,N',N'-tetraacetic acid; and 7,19,30-trioxa-1,4,10,13,16,22,27,33-octaazabicyclo[11,11,11] pentatriacontane hexahydrobromide.

Most preferably, the chelators for use in the present invention may include ethylenediamine-N,N,N',N'-tetraacetic acid (EDTA); the disodium salt of EDTA; 1,3-diaminopropane-N,N,N',N'-tetraacetic acid; and O,O'-bis(2-aminoethyl)ethyleneglycol-N,N,N',N'-tetraacetic acid.

Many antifungal agents are known to those of skill in the art and may be useful in the present invention. For example, antifungal agents contemplated for use in the present invention include, but are not limited to, new third generation triazoles such as UK 109,496 (Voriconazole); SCH 56592; ER30346; UK 9746; UK 9751; T 8581; and Flutrimazole; cell wall active cyclic lipopeptides such as Cilofungin LY121019; LY303366 (Echinocandin); and L-743872 (Pneumocandin); allylamines such as Terbinafine; imidazoles such as Omoconazole, Ketoconazole, Terconazole, Econazole, Itraconazole and Fluconazole; polyenes such as Amphotericin B, Nystatin, Natamycin, Liposomal Amphotericin B, and Liposomal Nystatin; and other antifungal agents including Griseofulvin; BF-796; MTCH 24; BTG-137586; RMP-7/Amphotericin B; Pradimicins (MNS 18184); Benanomicin; Ambisome; ABLC; ABCD; Nikkomycin Z; and Flucytosine.

More preferably, the antifungal agents for use in conjunction with the present invention may include polyenes such as Amphotericin B, Nystatin, Natamycin, Liposomal Amphotericin B, and Liposomal Nystatin; cell wall active cyclic lipopeptides such as Cilofungin LY121019; LY303366 (Echinocandin); and L-743872 (Pneumocandin); and other antifungal agents including Griseofulvin and Flucytosine.

Most preferably, the antifungal agents for use in the present invention may include Amphotericin B, Nystatin, Liposomal Amphotericin B, and Liposomal Nystatin.

The present invention also provides an effective method of treating a systemic fungal infection comprising the steps of obtaining a therapeutically effective amount of a pharmaceutical composition comprising at least one chelator operatively attached to a monoclonal antibody, at least one antifungal agent and a pharmaceutical excipient, diluent or adjuvant, and administering said pharmaceutical composition to a patient having a fungal infection. The monoclonal antibody is chosen to bind to a specific fungal antigen, and may be prepared according to any known method. The chelators and antifungal agents may be chosen from those indicated above.

Monoclonal antibodies useful in conjunction with the present invention are those that are specific for a targeted species of fungus. In preferred embodiments, the monoclonal antibodies are operatively attached to chelators. For the purposes of this disclosure, the phrase "a monoclonal antibody" denotes one or more monoclonal antibodies. As used herein, the term "monoclonal antibody" is defined as an antibody derived from a single clone of a B lymphocyte. Furthermore, as used herein, the term "operatively attached" connotes a chemical bond, either covalent or ionic, between the monoclonal antibody and chelator. As used herein, the term "specific" indicates that a chemical site on the monoclonal antibody will recognize and bind with a complementary chemical site on the surface of the cell of at least the fungal pathogen of interest.

The pharmaceutical compositions of the invention are provided to a patient having a fungal infection in an amount sufficient to exert a fungicidal or fungistatic effect upon fungi contacted by the composition. It will be understood with benefit of this disclosure that such dosages may vary considerably according to the patient, the infection presented by the patient, and the particular active ingredients comprising the pharmaceutical composition.

The antifungal agents of the present invention may be administered to a patient in an amount ranging from about 0.001 milligrams per kilogram of body weight per day to about 1000 mg per kg per day, including all intermediate dosages therebetween. It will be readily understood that "intermediate dosages", in these contexts, means any dosages between the quoted ranges, such as about 0.001, 0.002, 0.003, etc.; 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 mg per kg per day, and including all fractional dosages therebetween.

More preferably, the antifungal agents of the present invention may be administered to a patient in an amount ranging from about 0.01 milligrams per kilogram of body weight per day to about 100 mg per kg per day, including all intermediate dosages therebetween. It will be readily understood that "intermediate dosages", in these contexts, means any dosages between the quoted ranges, such as about 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 60, 70, 80, 90, and about 100 mg per kg per day, and including all fractional dosages therebetween.

Most preferably, the antifungal agents of the present invention may be administered to a patient in an amount ranging from about 0.1 milligrams per kilogram of body weight per day to about 10 mg per kg per day, including all intermediate dosages therebetween. It will be readily understood that "intermediate dosages", in these contexts, means any dosages between the quoted ranges, such as about 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9 and about 10 mg per kg per day, and including all fractional dosages therebetween.

The chelators of the present invention may be administered to a patient in an amount ranging from about 0.001 milligrams per kilogram of body weight per day to about 1000 mg per kg per day, including all intermediate dosages therebetween. It will be readily understood that "intermediate dosages", in these contexts, means any dosages between the quoted ranges, such as about 0.001, 0.002, 0.003, etc.; 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6,2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 mg per kg per day, and including all fractional dosages therebetween.

More preferably the chelators of the present invention may be administered to a patient in an amount ranging from about 0.01 milligrams per kilogram of body weight per day to about 100 mg per kg per day, including all intermediate dosages therebetween. It will be readily understood that "intermediate dosages", in these contexts, means any dosages between the quoted ranges, such as about 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 60, 70, 80, 90, and about 100 mg per kg per day, and including all fractional dosages therebetween.

Most preferably the chelators of the present invention may be administered to a patient in an amount ranging from about 0.1 milligrams per kilogram of body weight per day to about 10 mg per kg per day, including all intermediate dosages therebetween. It will be readily understood that "intermediate dosages", in these contexts, means any dosages between the quoted ranges, such as about 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, and about 10 mg per kg per day, and including all fractional dosages therebetween.

The monoclonal antibodies operatively attached to chelators may be administered to a patient in an amount ranging from about 0.001 milligrams per kilogram of body weight per day to about 1000 mg per kg per day, including all intermediate dosages therebetween. It will be readily understood that "intermediate dosages", in these contexts, means any dosages between the quoted ranges, such as about 0.001, 0.002, 0.003, etc.; 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2,2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 mg per kg per day, and including all fractional dosages therebetween.

More preferably, the monoclonal antibodies operatively attached to chelators may be administered to a patient in an amount ranging from about 0.01 milligrams per kilogram of body weight per day to about 100 mg per kg per day, including all intermediate dosages therebetween. It will be readily understood that "intermediate dosages", in these contexts, means any dosages between the quoted ranges, such as about 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 60, 70, 80, 90, and about 100 mg per kg per day, and including all fractional dosages therebetween.

Most preferably, the monoclonal antibodies operatively attached to chelators may be administered to a patient in an amount ranging from about 0.1 milligrams per kilogram of body weight per day to about 10 mg per kg per day, including all intermediate dosages therebetween. It will be readily understood that "intermediate dosages", in these contexts, means any dosages between the quoted ranges, such as about 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, and about 10, and including all fractional dosages therebetween.

The pharmaceutical compositions of the present invention may be administered by any known route, including parenterally and otherwise. This includes oral, nasal (via nasal spray or nasal inhaler), buccal, rectal, vaginal or topical administration. Administration may also be by orthotopic, intradermal subcutaneous, intramuscular, intraperitoneal or intravenous injection and/or infusion. Such compositions may be administered as pharmaceutically acceptable compositions that include pharmacologically acceptable carriers, buffers or other excipients. The phrase "pharmacologically acceptable" refers to molecular entities and compositions that do not produce an adverse, allergic or other untoward reaction when administered to a human. For treatment of conditions of the lungs, the preferred route is aerosol delivery to the lung via bronchoalveolar lavage or the like.

When administration of the pharmaceutical compositions of the present invention via intravenous injection and/or infusion is the preferred route, the pharmaceutical compositions of the present invention should administered gradually over a period of time ranging from 0.001 h to 100 h. More preferably, when administration of the pharmaceutical compositions of the present invention via intravenous injection and/or infusion is the preferred route, the pharmaceutical compositions of the present invention should administered gradually over a period of time ranging from 0.1 h to 50 h. Most preferably, when administration of the pharmaceutical compositions of the present invention via intravenous injection and/or infusion is the preferred route, the pharmaceutical compositions of the present invention should administered gradually over a period of time ranging from 1 h to 10 h.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1, FIG. 2, FIG. 3, FIG. 4, FIG. 5, FIG. 6, FIG. 7, FIG. 8, FIG. 9, FIG. 10 and FIG. 11 display plots of microbial population vs. time for cultures of species of Aspergillus, Candida and Fusarium. Response of these cultures to treatment with antimicrobials, chelators, and combinations thereof are indicated.

FIG. 1 shows the inhibitory effect of EDTA on *Apergillus flavus* in vitro.

FIG. 2 shows the inhibitory effect of EDTA on *Aspergillus terreus* in vitro.

FIG. 3 shows the inhibitory effect of EDTA on *Fusarium oxysporum* in vitro.

FIG. 4 shows the inhibitory effect of EDTA on *Candida krusei* in vitro.

FIG. 5 shows the synergistic inhibition of *Aspergillus fumigatus* by Amphotericin B and EDTA (1.0 mg/mL) in vitro.

FIG. 6 shows the synergistic inhibition of *Aspergillus fumigatus* by Amphotericin B and EDTA (0.1 mg/mL) in vitro.

FIG. 7 shows the synergistic inhibition of *Aspergillus flavus* by Amphotericin B and EDTA (1.0 mg/mL) in vitro.

FIG. 8 shows the synergistic inhibition of *Aspergillus flavus* by Amphotericin B and EDTA (0.1 mg/mL) in vitro.

FIG. 9 shows the synergistic inhibition of *Fusarium solani* by Amphotericin B and EDTA in vitro.

FIG. 10 shows the synergistic inhibition of *Aspergillus fumigatus* by Ambisome and EDTA (0.1 mg/mL) in vitro.

FIG. 11 shows the synergistic inhibition of *Fusarium solani* by Ambisome and EDTA in vitro.

DESCRIPTION OF ILLUSTRATIVE EMBODIMENTS

I. FUNGAL INFECTIONS

Figure 1:
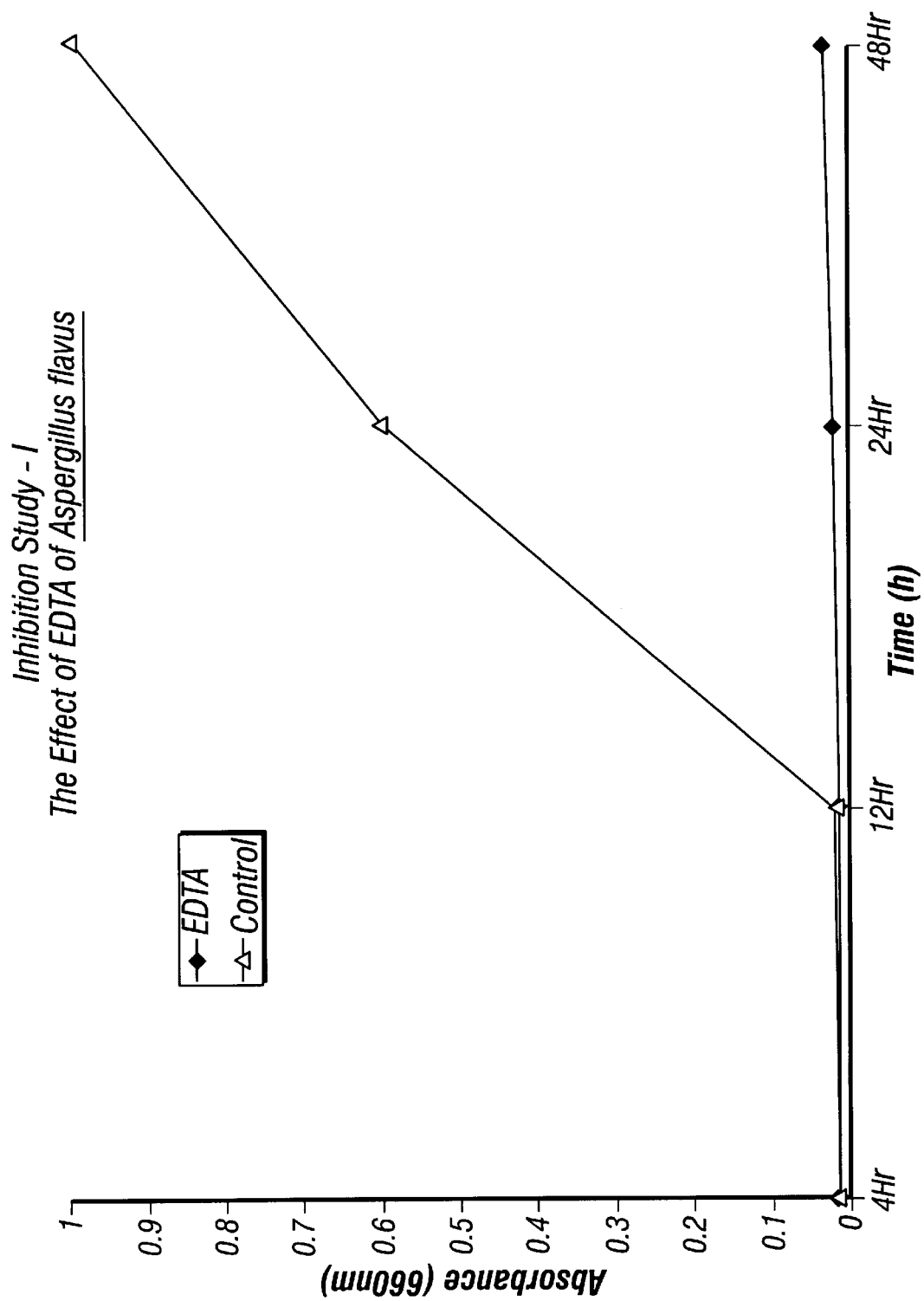

Infection is believed to be the cause of death in almost half of all patients who die of lymphoma, and in almost three quarters of patients who die of leukemia. Although bacteria are the causative organisms of many such infections, fungi also play a major role in these infection-related mortalities. As noted in the Background section, species of Candida, Aspergillus, and Fusarium are the major causes of fungal infection-related deaths in patients with leukemia and lymphoma. Additionally, fungal infection is a major cause of mortality in patients with congenital and acquired deficiencies of the immune system.

In their usual role as saprophytes on decaying vegetation, Aspergillus organisms are not contagious. Infection arises when spores of these ubiquitous fungi are aerosolized in the abiotic environment. No underlying predisposition of race, age, or sex leads to the development of Aspergillus infection.

Although Aspergillus infection can be acquired in the community, the largest threat to the immunocompromised patient is exposure to contaminated air in the hospital environment. Patients who have undergone open heart surgery, who have undergone organ or bone marrow transplantation, or who have prolonged neutropenia after anticancer chemotherapy may acquire life-threatening infection either on the wards where they are housed (domiciliary exposure) or when they are taken to the operating theater, radiology suite, or catheterization laboratory for an essential procedure (nondomiciliary exposure). Construction in the hospital, which results in the liberation of large numbers of spores into the immediate environment, is particularly hazardous for these patients (Rubin, 1994; Wade, 1994). Although there is considerable genetic heterogeneity among Aspergillus strains in nature, newly developed molecular typing systems have shown that patients are usually infected with a single strain, a finding that allows the clinician to rapidly assess whether two or more cases are from the same environmental source (Birch et al., 1995).

Several species of Aspergillus are known to cause invasive sinopulmonary infections in seriously immunocompromised patients. Following inhalation of spores, clinical aspergillosis can occur in three major presentations. The first presentation, allergic bronchopulmonary aspergillosis, develops when Aspergillus species colonize the bronchial tree and release antigens that cause a hypersensitivity pneumonitis. The second presentation, aspergilloma or "fungus ball," develops in pulmonary cavities, often in concert with other lung diseases such as tuberculosis. The third form, invasive pulmonary or disseminated aspergillosis, is a life threatening infection with a very high mortality rate.

The present invention provides pharmaceutical compositions and methods for the prevention and treatment of disseminated fungal infections. It is contemplated that the preparations of the invention will be useful in eliminating or inhibiting all types of fungal infections, providing so-called fungicidal or fungistatic effects. For example, the inventors have discovered that chelators have significant growth inhibitory effect against species of Aspergillus (see data in FIG. 1, FIG. 2, FIG. 3 and FIG. 4). The inventors have further demonstrated conclusively and unexpectedly that, when combined with antifungal agents, chelators show additive to synergistic inhibitory activity against the growth of fungal pathogens (see data in FIG. 5, FIG. 6, FIG. 7, FIG. 8, FIG. 9, FIG. 10 and FIG. 11). These discoveries provide the basis for a program of prevention and treatment of systemic fungal infections using any of several embodiments of the inventive pharmaceutical formulations, which may comprise various combinations of chelators, antifungal agents, and any necessary excipients, diluents or adjuvants.

In another aspect, the pharmaceutical formulations provided herein comprise chelators chemically bound, covalently, ionically or otherwise, to monoclonal antibodies which bind to the fungal antigen to be treated. Advantageously, the monoclonal antibodies may serve to deliver the attached chelators directly to their intended fungal targets, where the chelators may then bind trace metals such as iron and calcium which might otherwise serve as fungal virulence factors. The inventors contemplate that this preferred embodiment even more effectively eliminates or inhibits fungal infections by decreasing the tendency of the chelators to bind trace metals with which they may come into contact outside of the immediate vicinity of the infection

II. CHELATORS

A chelate is the type of coordination compound in which a central metal ion is attached by coordinate links to two or more nonmetal atoms in the same molecule. Heterocyclic rings are thus formed during chelation, with the metal atom as part of the ring. The molecule comprising the nonmetal linking atoms is termed a chelator. Chelators are used in various chemical applications, for example as titrating agents or as metal ion scavengers. Chelators can be used to remove ions from participation in biological reactions. For example, the well-known chelator ethylenediamine-N,N,N', N',-tetraacetic acid (EDTA) acts as an anticoagulant because it is capable of scavenging calcium ions from the blood.

It is known that iron and other trace metals are essential in the life cycle of microorganisms such as fungi. Without these trace metals, fungi are unable to grow and reproduce. Although iron is abundant in nature, its availability for microbial assimilation is limited owing to the insolubility of ferric ions at neutral or alkaline pH. As a consequence, many fungi have evolved their own specialized trace metal-scavenging molecules, called siderophores, which bind with trace metals and make them available for uptake by the fungi. The chelators used in conjunction with the present invention provide an inhibitory effect upon fungal pathogens by competing with the fungal siderophores for any available trace metal ions. In this way, the chelators present in the pharmaceutical preparations of the invention "steal" the metal ions essential for fungal growth, effectively causing the fungus to "starve to death." The added antifungal agents and/or monoclonal antibodies of the preparations of the invention can then come in and attack the weakened fungi, thereby destroying them or inhibiting their growth.

Figure 2:
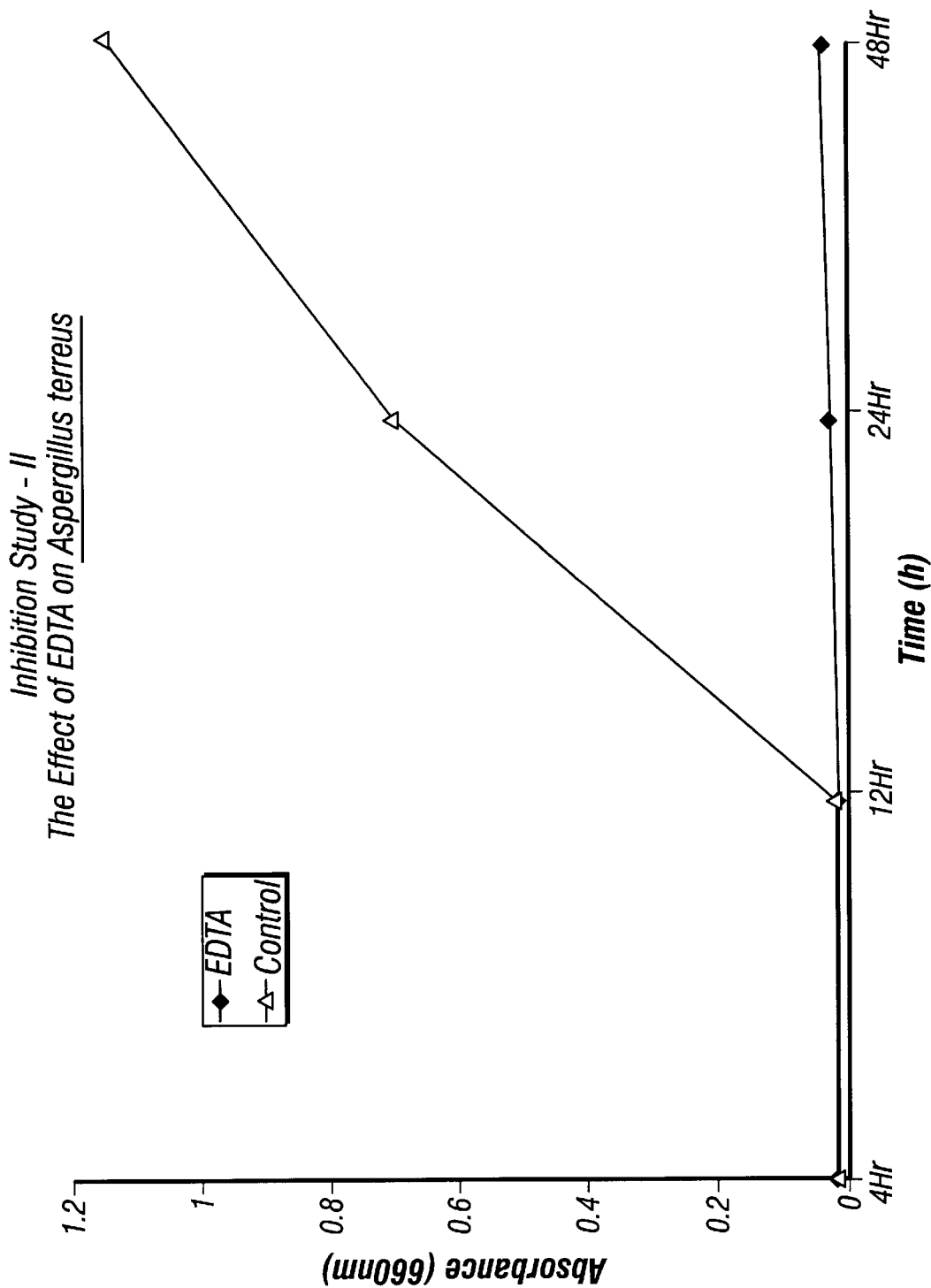
Figure 3:
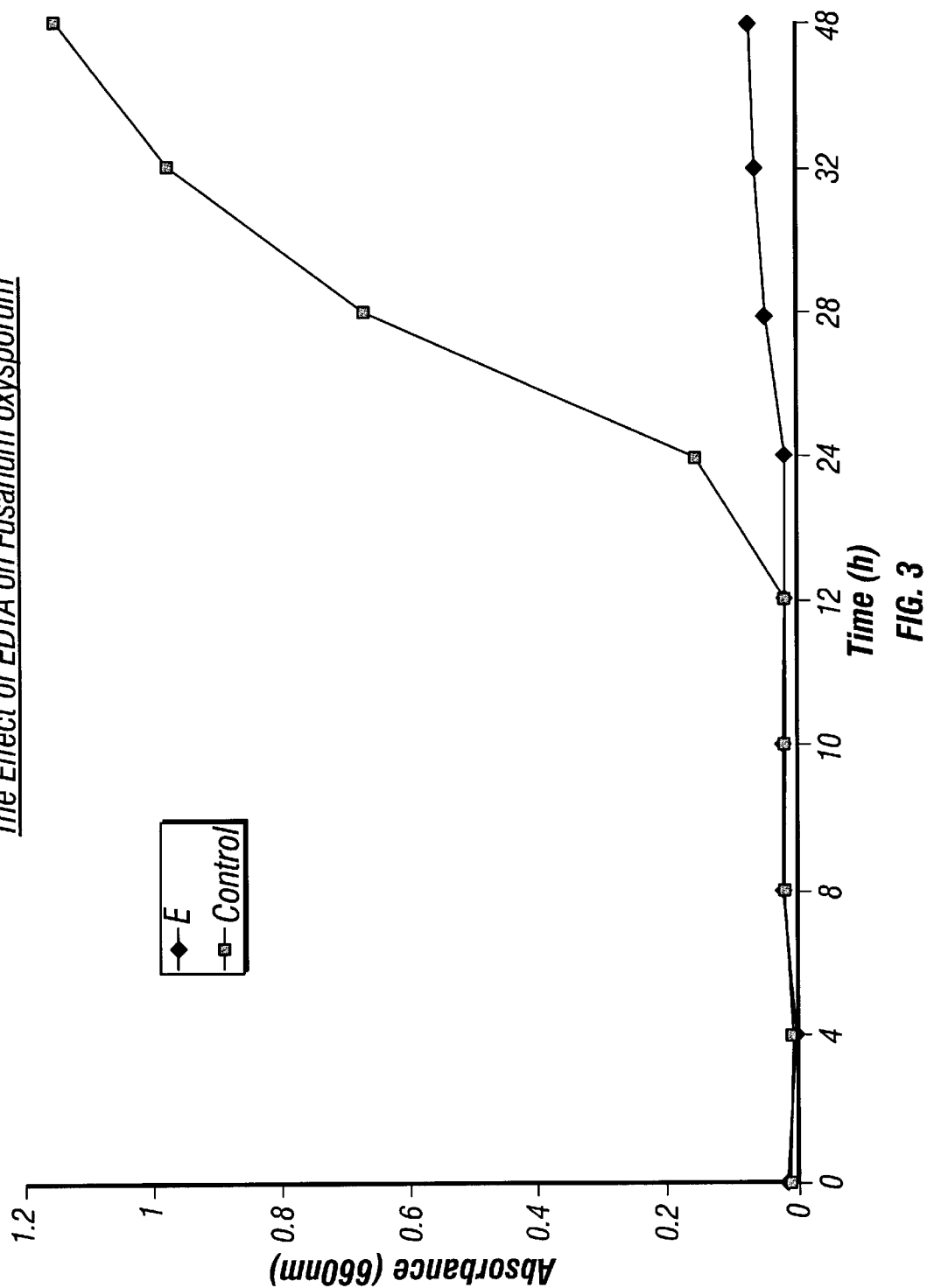
Figure 4:
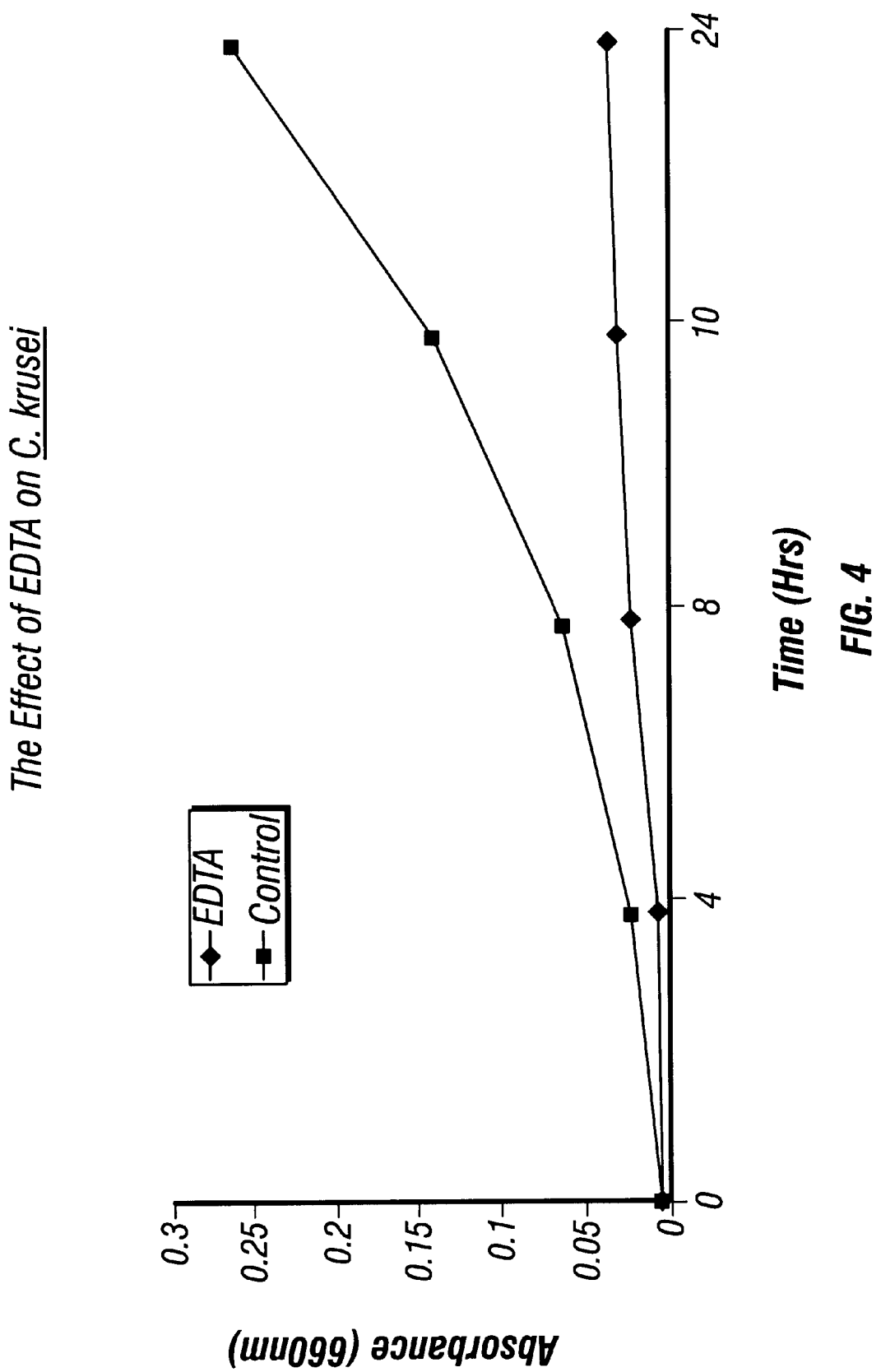
Figure 5:
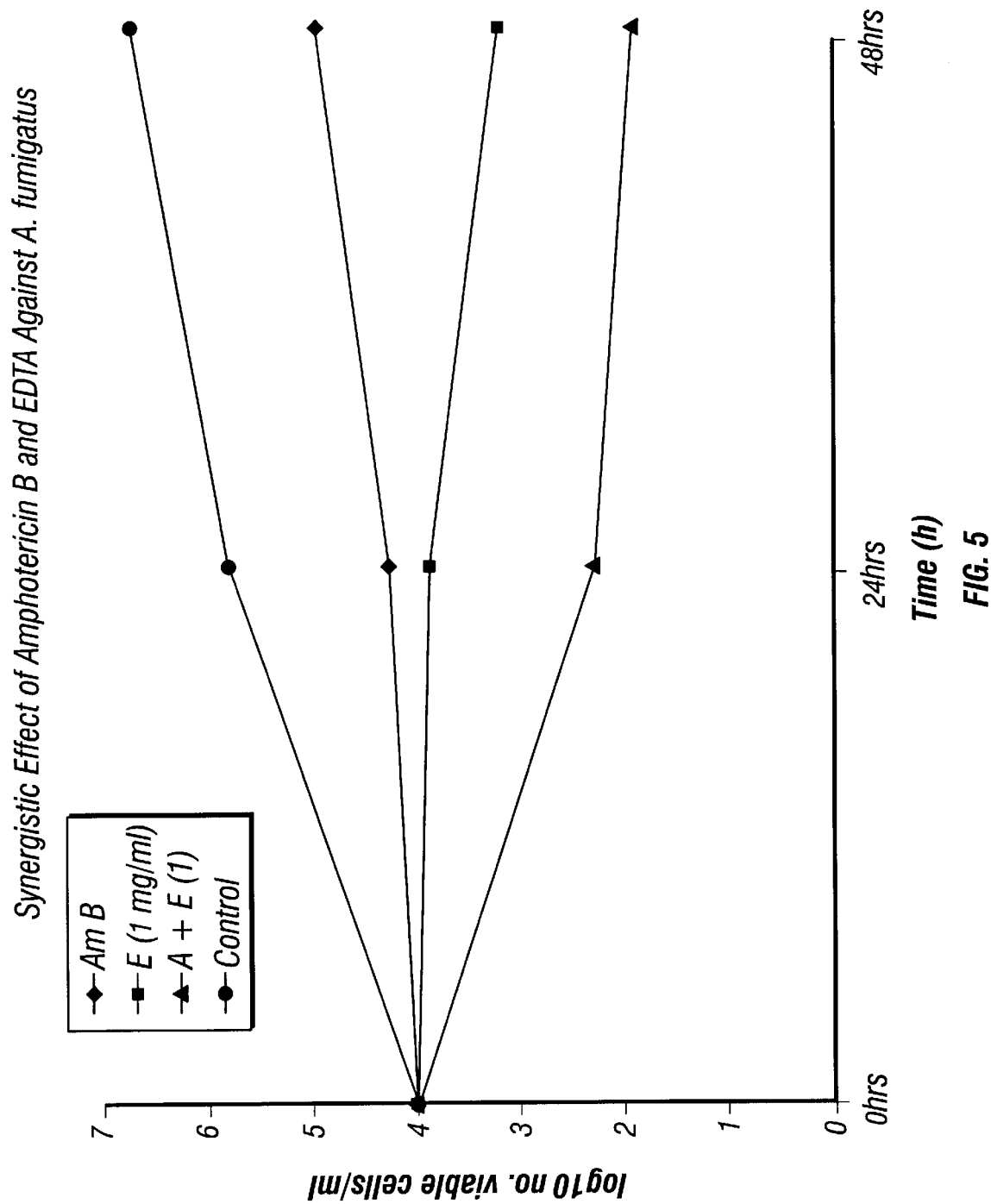

The inventors have discovered that the chelators of the present invention have significant growth inhibitory effect against species of Aspergillus. Referring to FIG. 1, it will be seen that EDTA exerts an inhibitory effect upon *Aspergillus flavus* relative to the control population. This effect is most clearly noticeable beginning 12 h after application of the chelator. Referring to FIG. 2 and FIG. 3, similar inhibitory behavior was noticed in cultures of *Aspergillus terreus* and *Fusarium oxysporum* following application of EDTA. The inhibitory effect of EDTA on *Candida krusei* is noticeable only a few hours after contact of the fungus with the chelator, as shown by FIG. 4.

Table 1 provides a representative list of chelators useful in conjunction with the present invention. The list provided in Table 1 is not meant to be exhaustive. Preferred chelators are those which bind trace metal ions with a binding constant ranging from $10^1$ to $10^{100}$; more preferred chelators are those which bind trace metal ions with a binding constant ranging from $10^{10}$ to $10^{80}$; most preferred chelators are those which bind trace metal ions with a binding constant ranging from $10^{15}$ to $10^{60}$. Also, preferred chelators are those which are readily attached to a monoclonal antibody, for example 1,3-diaminopropane-N,N,N',N'-tetraacetic acid (DTPA). Furthermore, preferred chelators are those which have been shown to have an inhibitory effect upon target fungal pathogens, for example the disodium salt of EDTA.

to its intended target, scavenging of any nearby trace metals which might otherwise serve as fungal virulence factors is assured.

Means for preparing and characterizing antibodies are well known in the art (See, e.g., *Antibodies: A Laboratory Manual*, Cold Spring Harbor Laboratory, 1988; incorporated herein by reference). The methods for generating monoclonal antibodies (MAbs) generally begin along the same

TABLE 1

CHELATORS

| ABBREVIATION | FULL NAME |
| --- | --- |
| EDTA free acid | Ethylenediamine-N,N,N',N',-tetraacetic acid |
| EDTA 2Na | Ethylenediamine-N,N,N',N',-tetraacetic acid, disodium salt, dihydrate |
| EDTA 3Na | Ethylenediamine-N,N,N',N',-tetraacetic acid, trisodium salt, trihydrate |
| EDTA 4Na | Ethylenediamine-N,N,N',N'-tetraacetic acid, tetrasodium salt, tetrahydrate |
| EDTA 2K | Ethylenediamine-N,N,N',N'-tetraacetic acid, dipotassium salt, dihydrate |
| EDTA 2Li | Ethylenediamine-N,N,N',N'-tetraacetic acid, dilithium salt, monhydrate |
| BDTA 2NH4 | Ethylenediamine-N,N,N'-tetraacctic acid, diammonium salt |
| EDTA 3K | Ethylenediamine-N,N,N',N'-tetraacetic acid, tripotassium salt, dihydrate |
| Ba(II)-EPTA | Ethylenediamine-N,N,N',N'-tetraa&etic acid, barium chelate |
| Ca(II)-EDTA | Ethylenediamine-N,N,N',N'-tetraacetic acid, calcium chelate |
| Ce(III)-EDTA | Ethylenediamine-N,N,N',N'-tetraacetic acid, cerium chelate |
| Co(II)-EDTA | Ethylenediamine-N,N,N',N'-tetraacetic acid, cobalt chelate |
| Cu(II)-EDTA | Ethylenediamine-N,N,N',N'-tetraacetic acid, copper chelate |
| Dy(III)-EDTA | Ethylenediamine-N,N,N',N'-tetraacetic acid, dysprosium chelate |
| Eu(III)-EDTA | Ethylenediamine-N,N,N',N'-tetraacetic acid, europium chelate |
| Fe(III)-EDTA | Ethylenediamine-N,N,N',N'-tetraacetic acid, iron chelate |
| In(III)-EDTA | Ethylenediamine-N,N,N',N'-tetraacetic acid, indium chelate |
| La(III)-EDTA | Ethylenediamine-N,N,N',N'-tetraacetic acid, lanthanum chelate |
| Mg(II)-EDTA | Ethylenediamine-N,N,N',N'-tetraacetic acid, magnesium chelate |
| Mn(II)-EDTA | Ethylenediamine-N,N,N',N'-tetraaceiic acid, manganese chelate |
| Ni(II)-EDTA | Ethylenediamine-N,N,N',N'-tetraacetic acid, nickel chelate |
| Sm(III)-EDTA | Ethylenediamine-N,N,N',N'-tetraacetic acid, samarium chelate |
| Sr(II)-EDTA | Ethylenediamine-N,N,N',N'-tetraacetic acid, strontium chelate |
| Zn(II)-EDTA | Ethylenediamine-N,N,N',N'-tetraacetic acid, zinc chelate |
| CyDTA | trans-1,2-Diaminocyclohexane-N,N,N',N'-tetraaceticacid, monohydrate |
| DHEG | N,N-Bis(2-hydroxyethyl)glycine |
| DTPA-OH | 1,3-Diamino-2-hydroxypropane-N,N,N',N'-tetraacetic acid |
| DTPA | 1,3-Diaminopropane-N,N,N',N'-tetraacetic acid |
| EDDA | Ethylenediamine-N,N'-diacetic acid |
| EDDP | Ethylenediamine-N,N'-dipropionic acid dihydrochloride |
| EDDPO | Ethylenediamine-N,N'-bis(methylenephosphonic acid), hemihydrate |
| EDTA-OH | N-(2-Hydroxyethyl)ethylenediamine-N,N',N'-triacetic acid |
| EDTPO | Ethylenediamine-N,N,N',N'-tetrakis(methylenephosponic acid) |
| EGTA | O,O'-bis(2-aminoethyl)ethyleneglycol-N,N,N',N'-tetraacetic acid |
| HBED | N,N-bis(2-hydroxybenzyl)ethylenediamine-N,N-diacetic acid |
| HDTA | 1,6-Hexamethylenediamine-N,N,N',N'-tetraacetic acid |
| HIDA | N-(2-Hydroxyethyl)iminodiacetic acid |
| IDA | Iminodiacetic acid |
| Methyl-EDTA | 1,2-Diaminopropane-N,N,N',N'-tetraacetic acid |
| NTA | Nitrilotriacetic acid |
| NTP | Nitrilotripropionic acid |
| NTPO | Nitrilotris(methylenephosphoric acid), trisodium salt |
| O-Bistren | 7,19,30-Trioxa-1,4,10,13,16,22,27,33-octaazabicyclo [11,11,11]pentatriacontane, hexahydrobromide |
| TTHA | Triethylenetetramine - N,N,N',N'',N''',N'''-hexaacetic acid |

III. MONOCLONAL ANTIBODIES

Monoclonal antibodies are antibodies derived from a single clone of B lymphocytes. As such, they are homogenous in structure and antigen specificity, making them useful as vectors for directing radionuclides, drugs, or toxins to tissues of interest such as malignant cells.

In one embodiment, the pharmaceutical formulations of the invention may comprise chelators chemically attached to monoclonal antibodies which have been designed to bind to the fungal antigen site of interest. Advantageously, the monoclonal antibodies may serve to deliver the attached chelators directly to their intended fungal targets, where the chelators may then bind trace metals which exist in the vicinity of the fungal cell. By delivering the chelator directly lines as those for preparing polyclonal antibodies. Briefly, a polyclonal antibody is prepared by immunizing an animal with an immunogenic composition and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA).

Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-diazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U. S. Pat. No. 4,196,265, incorporated herein by reference. Typically, this technique involves immunizing a suitable animal with a selected immunogen composition, e.g., a purified or partially purified administration of approximately $10^6$ *Aspergillus fumigatus* conidia (or other species, such as *Aspergillus flavus, Aspergillus terreus, Candida krusei*, or *Fusarium solani*, or any other fungal pathogen known to affect humans) in 1.0 mL of sterile NaCl solution with 1.0 mL of Freund's incomplete adjuvant. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

The inventors also contemplate the use of a molecular cloning approach to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

IV. ATTACHMENT OF CHELATORS TO MONOCLONAL ANTIBODIES

Methods for attachment of chelators to proteins, including monoclonal antibodies, are well known in the art. One of the earliest efforts at attachment of metal-binding groups to proteins was that of Gelewitz et al. (1954) who coupled azo-phenanthroline and azo-oxine to albumin; attempts were made to analyze the products by colorimetric titration with iron. Later, Sokolovsky et al., (1967) converted lysozyme tyrosine to 3-aminotyrosine, and discussed the potential of this procedure to yield new heavy-atom derivatives for x-ray crystallography. Benisek and Richards (1968) explored the use of picolinimidate to produce metal-binding sites on proteins, with a similar goal.

The first chelate-protein conjugates that were stable enough for use in vivo were the protein azophenyl-EDTAs of Sundberg et al. (1974) which resulted from the initial ideas of Baldeschwieler [Meares et al. (1984)]. Those protein azophenyl-EDTA compounds were studied over the years 1974–1979, during which the basic requirements of protein-chelate directed toward in vivo use were explored (Goodwin et al., 1975; Meares et al., 1976; Leung et al., 1978; DeRiemer et al., 1979).

In 1976, Krejcarek and Tucker activated DTPA by a mixed anhydride method and coupled it to albumin (Krejcarek and Tucker, 1976). The product bound $^{111}$In stably enough for many applications in vivo, and has been used by many nuclear medicine researchers since (Khaw et al., 1980; Scheinberg, 1982). The procedure was subsequently improved by Hnatowich et al. (1983). Comparison of the stability of $^{111}$In complexes in human serum under physiological conditions shows that the indium is lost from DTPA complexes much more rapidly than from phenyl-EDTA complexes, whether bound to a protein or not (Yeh et al., 1979). However, $^{111}$In-DTPA complexes decompose slowly enough so that they are useful in many diagnostic procedures, including those involving antibodies.

By 1979, a general method for converting a-amino acids to bifunctional chelating agents had been devised (Yeh et al., 1979). This has permitted the synthesis of a wide range of structures from materials with an interesting choice of useful sidechains.

Typically, an amino acid such as L-phenylalanine is nitrated, esterified, and allowed to react with an amine $RNH_2$. If R=H, the final product will be an EDTA analog, whereas if R=$H_2NCH_2CH_2$—, the final product will be a DTPA analog. The amide is reduced, and the amines are carboxymethylated to form a chelating group, and then the aromatic nitro group is reduced to an amine. This aromatic amine can be further modified in several ways to form useful derivatives. For example, treatment with nitric acid renders a diazonium compound which may react with several different amino acid residues.

As noted above, in embodiments of the invention where the chelator is operatively attached to a monoclonal antibody, it is contemplated that such attachment may be by either covalent or ionic bond. One example of such an attachment is the diazophenyl coupling described above, but any other means of chemically binding a chelator to a monoclonal antibody may be used.

V. ANTIFUNGAL AGENTS

Fungal infections and the drugs used to treat them have traditionally been divided into two classes: superficial and systemic. This distinction is becoming increasingly arbitrary, however, as some of the drugs previously used to treat only one class of infection or the other are now used in both cases, with the differences being ones of mode of administration and/or concentration of active ingredient. Also, some infections, for example superficial mycoses, may now be treated either systemically or topically.

The classes of drugs used currently to treat systemic fungal infections include the polyenes, the imidazoles and triazoles, griseofulvin, and flucytosine. The polyenes bind to ergosterols in fungal membranes, resulting in the formation of transmembrane channels which allow the escape of metabolites essential to maintaining the viability of the fungal cell. Polyenes are highly toxic. The imidazoles and triazoles are structurally related and share the same antifungal spectrum and mechanism of action, namely the inhibition of the fungal sterol 14-α-demethylase enzyme system. Griseofulvin was isolated from a species of Penicillium and acts by inhibiting fungal mitosis. Flucytosine is a fluorinated pyrimidine which acts upon fungi by inhibiting thymidylate synthetase.

In addition to the above well-known classes of antifungal agents, some compounds more traditionally thought of as antibacterial agents, for example minocycline (a tetracycline derivative), have been demonstrated to have a fungistatic or fungicidal effect on the surface of a venous catheter when administered in combination with a chelator, for example EDTA, and other compounds. See, for example, U.S. Pat. No. 5,362,754 by Raad et al., or U.S. patent application Ser. No. 08/317,309 by Raad et al., both of which are herein incorporated by reference.

Figure 6:
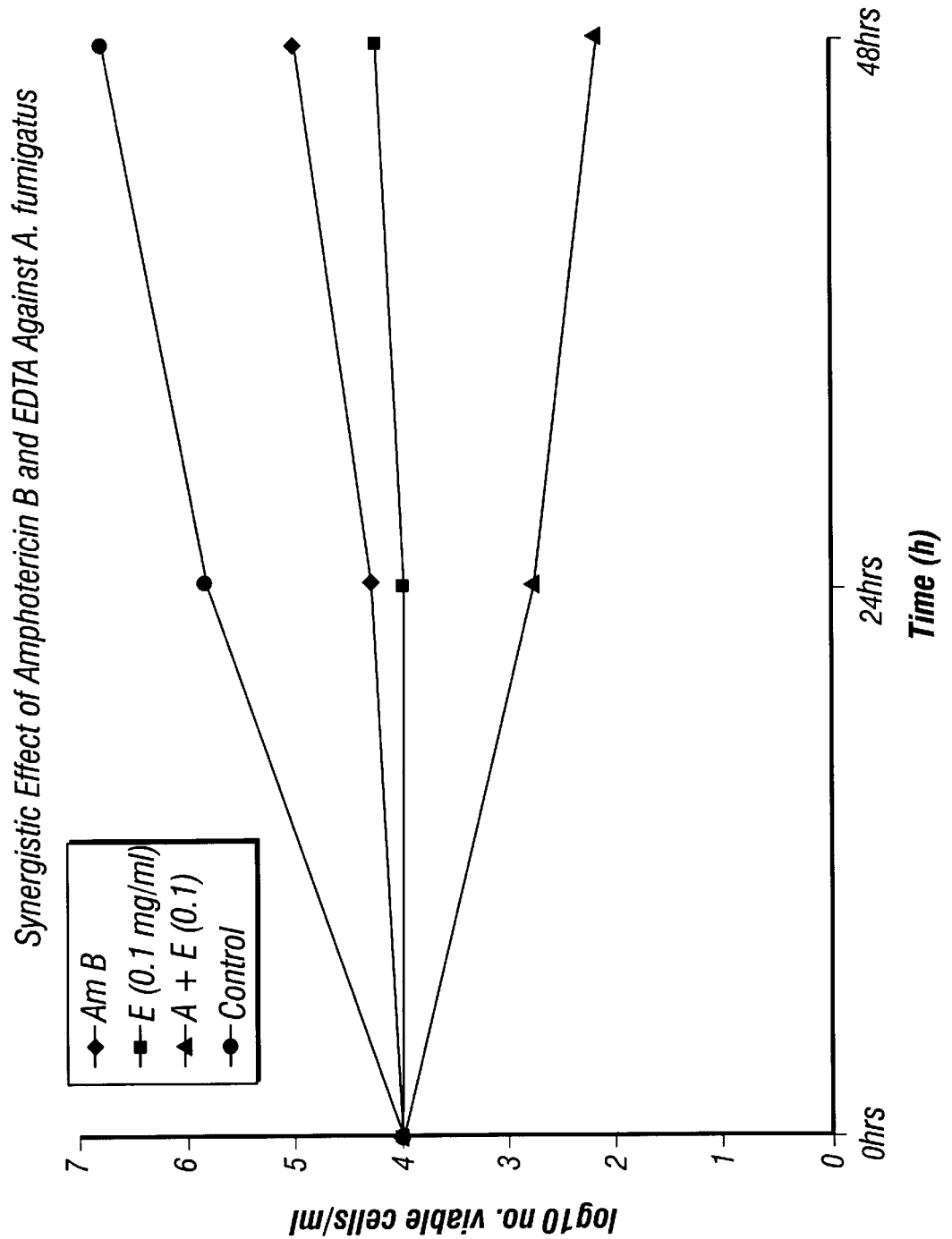
Figure 7:
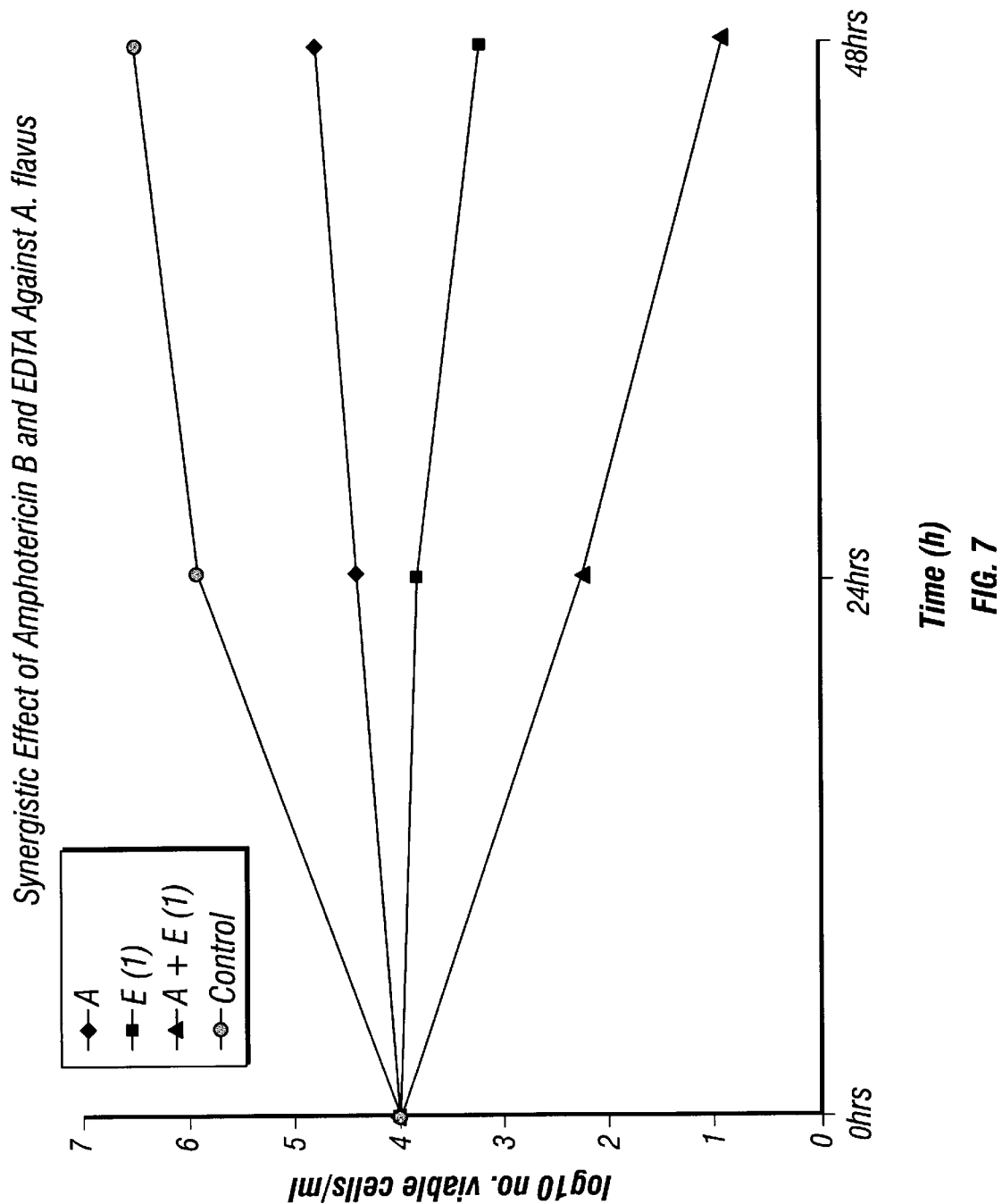
Figure 8:
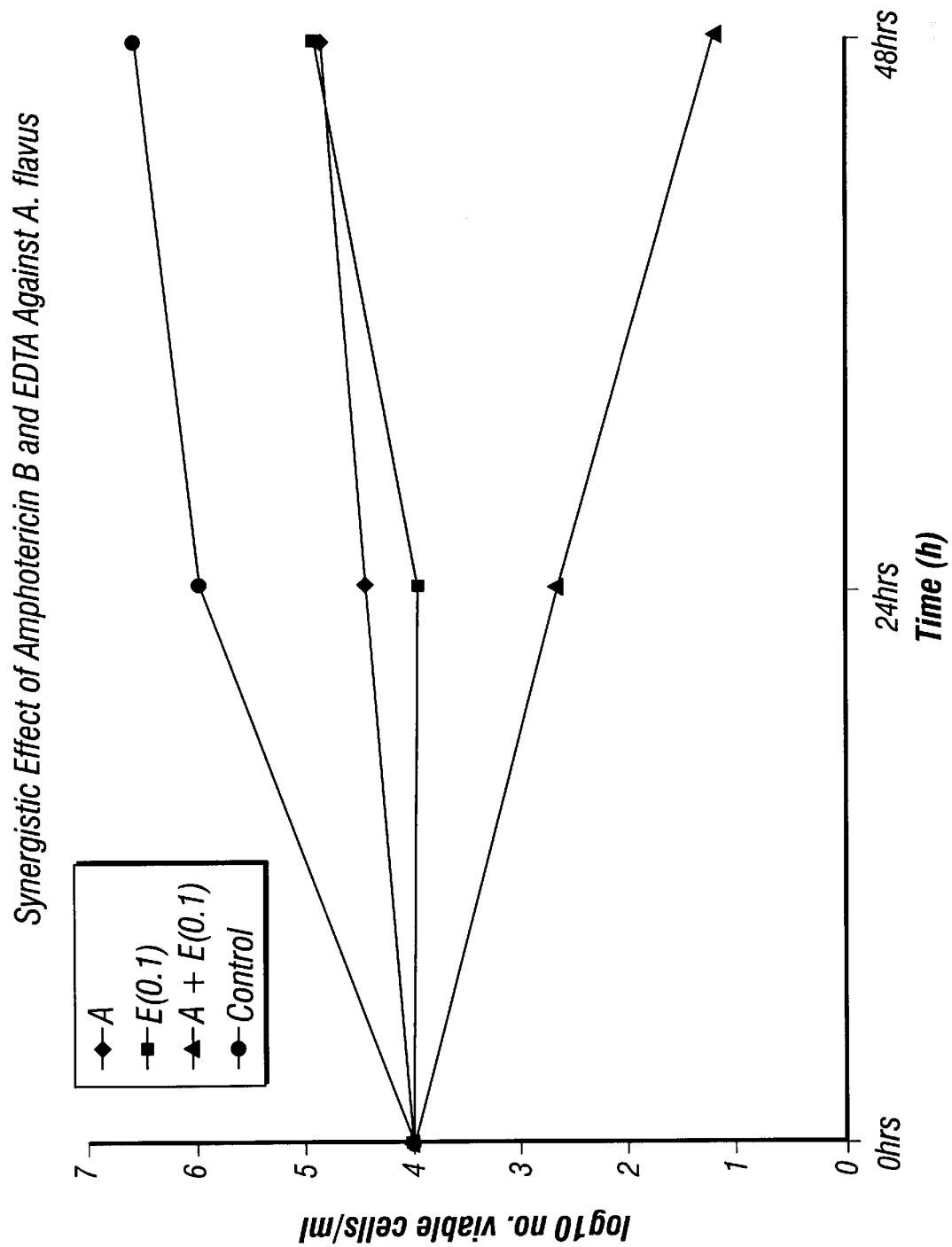
Figure 9:
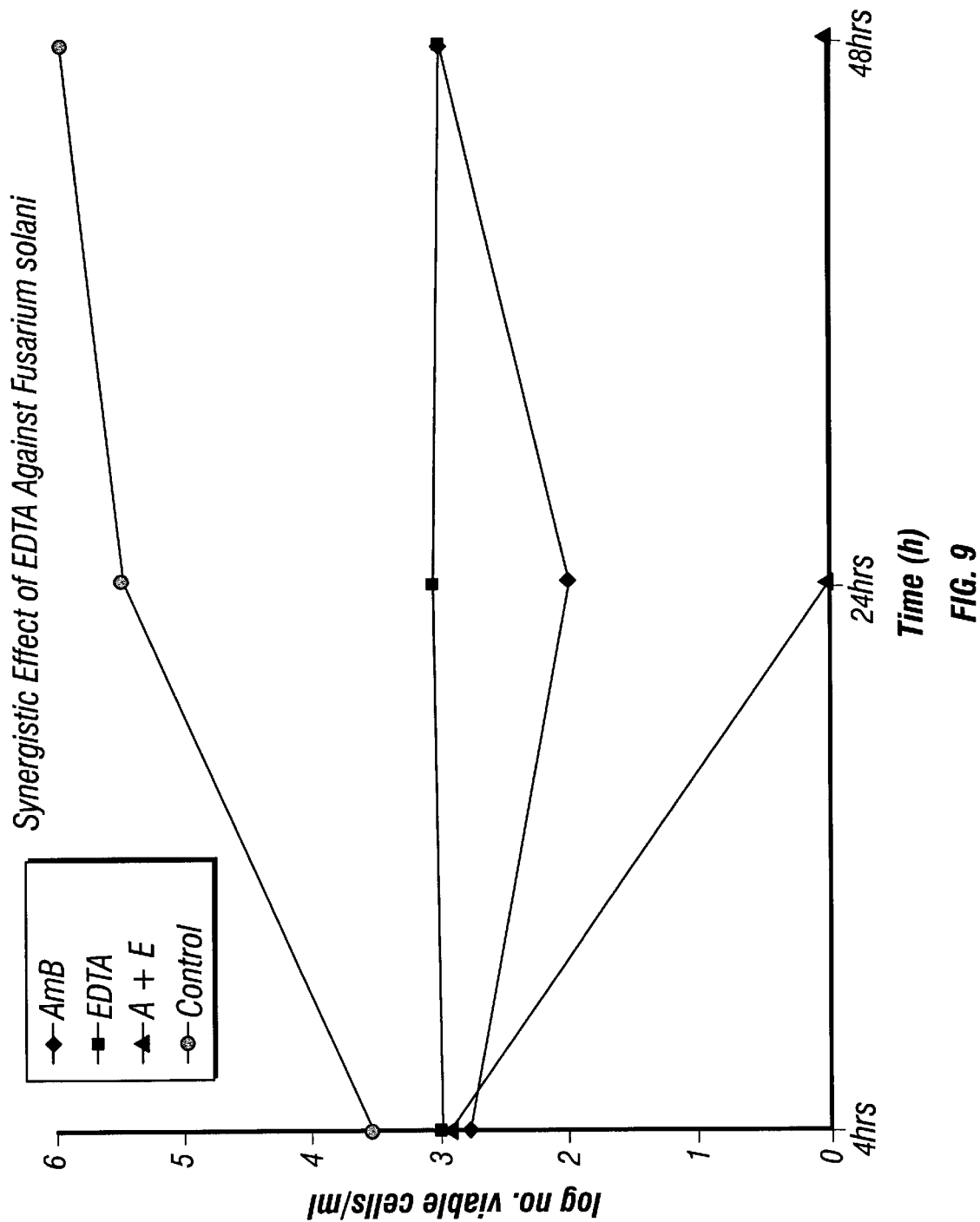

Antifungal agents particularly preferred in connection with the present invention include the polyenes, most preferably Amphotericin B and liposomal Amphotericin B. The inventors have demonstrated that Amphotericin B acts synergistically in concert with the chelator EDTA to inhibit species of Aspergillus and Fusarium. A drug combination is said to exhibit synergism when the combination achieves a desired effect one order of magnitude or greater than the analogous effect of the most potent individual constituent of the combination. For example, referring to FIG. 5, Amphotericin B at a concentration of 1 μg/mL and EDTA at a concentration of 1 mg/mL act synergistically to inhibit the growth of *Aspergillus fumigatus* by a margin of almost two orders of magnitude relative to EDTA acting alone. The same effect is observed when the concentration of EDTA is reduced to 0.1 mg/mL (FIG. 6). Likewise, Amphotericin B and EDTA inhibit *Aspergillus flavus* synergistically, whether EDTA is present at 1.0 mg/mL or 0.1 mg/mL (FIG. 7 and FIG. 8). This synergism extends to inhibition of *Fusarium solani* as well, as seen in FIG. 9. FIG. 10 and FIG. 11 show the synergistic inhibitory effect of liposomal Amphotericin B and EDTA against *A. fumigatus* and *F. solani*.

The inventors have demonstrated, remarkably and for the first time, that the chelators and antifungal agents of the present invention act together in a synergistic fashion to inhibit fungal pathogens. It is contemplated that as a consequence of this synergism described above between the chelators and the antifungal agents of the present invention, decreased dosages of antifungal agent will be sufficient to induce a fungicidal effect in a patient with a fungal infection, relative to the dosage required when administering an antifungal agent alone. Advantageously, a decreased dosage of antifungal agent, when used in conjunction with the chelators of the present invention, will serve to minimize any undesirable side effects which antifungal agents may induce in patients to whom they are administered.

Table 2 provides a representative list of antifimgal agents useful in conjunction with the present invention. The list provided in Table 2 is not meant to be exhaustive.

TABLE 2

| ANTIFUNGAL AGENTS | |
|---|---|
| UK 109,496 (Voriconazole) | Terbinafine |
| SCH 56592 | BF-796 |
| ER30346 | MTCH 24 |
| UK 9746 | BTG-137586 |
| UK 9751 | RMP-7/ Amphotericin B |
| T 8581 | Omoconazole |
| Flutrimazole | Amphotericin B |
| Cilofungin LY121019 | Nystatin |
| LY303366 (Echinocandin) | Natamycin |
| L-743872 (Pneumocandin) | Clotrimazole |
| Pradimicins (MNS 18184) | Miconazole |
| Benanomicin | Ketoconazole |
| Ambisome | Terconazole |
| ABLC | Econazole |
| Liposomal Amphotericin | Itraconazole |
| ABCD | Fluconazole |
| Liposomal Nystatin | Griseofulvin |
| Nikkomycin Z | Flucytosine |

VI. PHARMACEUTICAL COMPOSITIONS AND ROUTES OF ADMINISTRATION

Pharmaceutical compositions of the instant invention comprise an effective amount of at least a chelator dissolved or dispersed in a pharmaceutically acceptable carrier, such as a pharmaceutically acceptable buffer, solvent or diluent, or aqueous medium. Pharmaceutical compositions of the instant invention may also comprise an 10 effective amount of a chelator and an antifungal agent dissolved or dispersed in a pharmaceutically acceptable carrier, such as a pharmaceutically acceptable buffer, solvent or diluent, or aqueous medium. Additionally, pharmaceutical compositions of the instant invention may comprise an effective amount of a chelator operatively attached to a monoclonal antibody dissolved or dispersed in a pharmaceutically acceptable carrier, such as a pharmaceutically acceptable buffer, solvent or diluent, or aqueous medium. Also, pharmaceutical compositions of the instant invention comprise an effective amount of a chelator operatively attached to a monoclonal antibody, as well as an antifungal agent, all dissolved or dispersed in a pharmaceutically acceptable carrier, such as a pharmaceutically acceptable buffer, solvent or diluent, or aqueous medium. Such compositions also can be referred to as inocula.

The phrases "pharmaceutically acceptable" or "pharmacologically acceptable" refer to molecular entities and compositions that do not produce an adverse, allergic or other untoward reaction when administered to a human. As used herein the terms "pharmaceutically acceptable carrier" and "pharmaceutically acceptable buffer, solvent or diluent" include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

As used herein the terms "contact", "contacted", and "contacting", are used to describe the process by which an effective amount of a pharmacological agent, e.g., any of the compounds disclosed in the present invention, comes in direct juxtaposition with the target cell.

For methods of treating mammals, pharmaceutical compositions may be administered by a variety of techniques, such as parenteral, topical or oral administration. For example, the compositions of the instant invention may also be formulated for parenteral administration, e.g., formulated for injection via the intravenous, intramuscular, subcutaneous, or even intraperitoneal routes. The preparation of an aqueous composition that contains one of the inventive compounds as an active ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be employed; and the preparations can also be emulsified.

Solutions of the inventive compositions as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters. Sterile powders for the extemporaneous preparation of sterile injectable solutions or dispersions may also be useful. In all cases the form must be sterile and must be fluid to the extent that easy syringability exists. It must be stable under the conditions of manufacture and storage and must be preserved against the contaminating action of microorganisms, such as bacteria and fungi.

The compositions of the instant invention may also be formulated into a composition in a neutral or salt form. Pharmaceutically acceptable salts include the acid addition salts (formed, e.g., with any free amino groups present), which are formed with inorganic acids such as, for example, hydrochloric or phosphoric acids, or such organic acids as acetic, oxalic, tartaric, mandelic, and the like. Salts formed with any free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compounds of the present invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variations in dosage will necessarily occur depending on the condition of the subject being treated. The person responsible for administration will, in any event, determine the appropriate dose for the individual subject.

VII. PREVENTION AND TREATMENT OF DISSEMINATED FUNGAL INFECTIONS

The pharmaceutical compositions of the invention will be provided to a patient having a fungal infection in an amount sufficient to exert a fungicidal or fungistatic effect upon fungal contacted by the composition. It will be understood with benefit of this disclosure that such dosages may vary considerably according to the patient, the infection presented by the patient, and the particular active ingredients comprising the pharmaceutical composition.

The antifungal agents of the present invention may be administered to a patient in an amount ranging from about 0.001 milligrams per kilogram of body weight per day to about 1000 mg per kg per day, including all intermediate dosages therebetween. It will be readily understood that "intermediate dosages", in these contexts, means any dosages between the quoted ranges, such as about 0.001, 0.002, 0.003, etc.; 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 mg per kg per day, and including all fractional dosages therebetween.

More preferably, the antifungal agents of the present invention may be administered to a patient in an amount ranging from about 0.01 milligrams per kilogram of body weight per day to about 100 mg per kg per day, including all intermediate dosages therebetween. It will be readily understood that "intermediate dosages", in these contexts, means any dosages between the quoted ranges, such as about 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 60, 70, 80, 90, and about 100 mg per kg per day, and including all fractional dosages therebetween.

Most preferably, the antifungal agents of the present invention may be administered to a patient in an amount ranging from about 0.1 milligrams per kilogram of body weight per day to about 10 mg per kg per day, including all intermediate dosages therebetween. It will be readily understood that "intermediate dosages", in these contexts, means any dosages between the quoted ranges, such as about 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9 and about 10 mg per kg per day, and including all fractional dosages therebetween.

The chelators of the present invention may be administered to a patient in an amount ranging from about 0.001 milligrams per kilogram of body weight per day to about 1000 mg per kg per day, including all intermediate dosages therebetween. It will be readily understood that "intermediate dosages", in these contexts, means any dosages between the quoted ranges, such as about 0.001, 0.002, 0.003, etc.; 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 mg per kg per day, and including all fractional dosages therebetween.

More preferably the chelators of the present invention may be administered to a patient in an amount ranging from about 0.01 milligrams per kilogram of body weight per day to about 100 mg per kg per day, including all intermediate dosages therebetween. It will be readily understood that "intermediate dosages", in these contexts, means any dosages between the quoted ranges, such as about 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 60, 70, 80, 90, and about 100 mg per kg per day, and including all fractional dosages therebetween.

Most preferably the chelators of the present invention may be administered to a patient in an amount ranging from about 0.1 milligrams per kilogram of body weight per day to about 10 mg per kg per day, including all intermediate dosages therebetween. It will be readily understood that "intermediate dosages", in these contexts, means any dosages between the quoted ranges, such as about 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, and about 10 mg per kg per day, and including all fractional dosages therebetween.

The monoclonal antibodies operatively attached to chelators may be administered to a patient in an amount ranging from about 0.001 milligrams per kilogram of body weight per day to about 1000 mg per kg per day, including all intermediate dosages therebetween. It will be readily understood that "intermediate dosages", in these contexts, means any dosages between the quoted ranges, such as about 0.001, 0.002, 0.003, etc.; 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9,2.0,2.1,2.2,2.3, 2.4,2.5,2.6,2.7, 2.8,2.9, etc.; 3,4,5,6,7,8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 mg per kg per day, and including all fractional dosages therebetween.

More preferably, the monoclonal antibodies operatively attached to chelators may be administered to a patient in an amount ranging from about 0.01 milligrams per kilogram of body weight per day to about 100 mg per kg per day, including all intermediate dosages therebetween. It will be readily understood that "intermediate dosages", in these contexts, means any dosages between the quoted ranges, such as about 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 60, 70, 80, 90, and about 100 mg per kg per day, and including all fractional dosages therebetween.

Most preferably, the monoclonal antibodies operatively attached to chelators may be administered to a patient in an amount ranging from about 0.1 milligrams per kilogram of body weight per day to about 10 mg per kg per day, including all intermediate dosages therebetween. It will be readily understood that "intermediate dosages", in these contexts, means any dosages between the quoted ranges, such as about 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, and about 10 mg per kg per day, and including all fractional dosages therebetween.

The pharmaceutical compositions of the present invention may be administered by any known route, including parenterally and otherwise. This includes oral, nasal (via nasal spray or nasal inhaler), buccal, rectal, vaginal or topical administration. Administration may also be by orthotopic, intradermal subcutaneous, intramuscular, intraperitoneal or intravenous injection and/or infusion. Such compositions may be administered as pharmaceutically acceptable compositions that include pharmacologically acceptable carriers, buffers or other excipients. The phrase "pharmacologically acceptable" refers to molecular entities and compositions that do not produce an adverse, allergic or other untoward reaction when administered to a human. For treatment of conditions of the lungs, the preferred route is aerosol delivery to the lung via bronchoalveolar lavage or the like.

VIII. PACKAGING AND KITS

The container means of the kits will generally include at least one vial, test tube, flask, bottle, syringe or other container means, into which the linked antibody/chelator may be placed, and preferably, suitably aliquoted. Where a second or third antifungal agent, other chelator, or additional component is provided, the kit will also generally contain a second, third or other additional container into which this component may be placed. The kits of the present invention will also typically include a means for containing the antibody/chelator, antifungal agent, other chelator, and any other reagent containers in close confinement for commercial sale. Such containers may include injection or blow-molded plastic containers into which the desired vials are retained.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synergy Study

The goal of this study was to determine if there is a synergistic effect between EDTA and Amphotericin B and EDTA and Ambisome respectively. The data collected are displayed in FIG. 5, FIG. 6, FIG. 7, FIG. 8, FIG. 9, FIG. 10 and FIG. 11. These figures are discussed elsewhere in the Detailed Description section. The studies were conducted in a laboratory incubator at a constant temperature of 30° C.

The medium was a single lot of liquid RPMI 1640 medium (Whittaker Bioproducts, Inc., Walkersville, Md.) supplemented with 0.3g of L-glutamine per liter and 0.165 M MOPS buffer (34.54 g/liter) and without sodium bicarbonate.

Test inocula contained approximately $1 \times 10^3$ to $1 \times 10^4$ conidia/mL. To induce conidium and sporangiophore formation, fungi were grown on sabouraud dextrose agar plates at 35° C. for 5 to 7 days. Each fungus was then covered with approximately 2 mL sterile 0.85% saline water. The suspension was then harvested by gently probing the colonies with sterile glass rods. The resulting mixture of conidia or sporangiophores and hyphal fragments was withdrawn and filtered through a sterile 4×4 gauze to a sterile tube. The homogenous suspension was later mixed with a vortex mixer for 30 s and the densities of the suspension were read and adjusted to a range of 80 to 85% transmittance. Inoculum of 0.1 mL was delivered to each flask containing 20 mL of RPMI and drug dilution series. The final conidia concentration ranged from $1 \times 10^3$ to $1 \times 10^4$ conidia/mL. A control flask was maintained without any drugs. The flasks were incubated in a shaker at 30° C. for 24 to 48 h. Glass beads were added to all flasks with visible fungal growth in an attempt to homogenize the solution and achieve even distribution of conidia for culture. Cultures were done at 0, 4, 24, and 48 h on sabouraud dextrose agar plates and incubated at 35° C. for 48 h.

Amphotericin B for injection, USP (Gensia Laboratories, LTD.) was suspended and diluted in sterile water and stored at 1 mg/mL in a glass vile in the dark at −70° C.

Ambisome was obtained in 50 mg vials and used immediately upon opening of the vial. Typically, 50 mg of Ambisome was diluted in 12 mL of sterile water. Further dilutions were performed as needed.

Edetate disodium INJ., USP (Abbott Laboratories, North Chicago, Ill.) was stored at a concentration of 150 mg/mL at 4° C.

Further dilutions were made to achieve the desired concentration of each drug at the time of the study. For Amphotericin B and Ambisome, the concentration was 1.0 µg/mL and for EDTA the concentrations were 0.1 and 1.0 mg/mL.

EXAMPLE 2

Inhibition Study

The goal of this study was to determine if chelators have an inhibitory effect on species of Aspergillus, Fusarium, and Candida. The data collected are displayed in FIG. 1, FIG. 2, FIG. 3 and FIG. 4. These figures are discussed elsewhere in the Detailed Description section. A spectrophotometer was used at a frequency of 660 nm to measure the absorbency of the solution.

For molds, all inocula were started at $1 \times 10^4$ conidia/mL. For yeast and bacteria, all inocula were started at $1 \times 10^6$ cfu/mL. The medium used was Mueller-Hinton.

The concentration of chelator in these studies was 0.35 mg EDTA per mL water.

EXAMPLE 3

In vivo Prophetic Model

In vivo studies will be conducted with either rabbits or mice, both of which are suitable animal models. Immunosupression with cyclophosphamide should be given intravenously 3 days prior to commencement of the study in order to achieve neutropenia by the day of animal infection.

Treatment with all drugs begins 18 to 24 h after infection and continues for 10 days.

All animals surviving to day 11 are sacrificed. Their lungs, kidneys, liver, and spleen are removed and transferred into 5 mL of sterile saline, homogenized in a tissue grinder for 15 to 30 sec, and diluted to $10^{-1}$, $10^{-2}$, $10^{-3}$, and $10^{-4}$. A total of 1.0 mL of each dilution is spread onto a sabouraud dextrose agar plate and allowed to grow by incubating them at 37° C. The plates are then counted for quantitative analysis. Also, histopathology analysis will be conducted on all organs analyzed.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Benisek and Richards, *J. Biol. Chem.*, 243:4267, 1968.
Campbell, In: *Monoclonal Antibody Technology, Laboratory Techniques in Biochemistry and Molecular Biology*, Vol. 13, Burden and Von Knippenberg, (Eds.), Amsterdam, Elseview, pp 75–83, 1984
DeRiemer, Meares, Goodwin, Diamanti, *J. Med. Chem.*, 22:019, 1979.
Gefter et al., *Somatic Cell Genet.*, 3:231–236, 1977.
Gelewitz, Riedemann, Klotz, *Arch. Biochem. Biophys.*, 53:411, 1954.
Goding, 1986, In: *Monoclonal Antibodies: Principles and Practice*, 2nd ed., Academic Press, Orlando, Fla., pp. 60–61, 65–66, 71–74, 1986.
Goodwin, Sundberg, Diamanti, Meares, In: *Radiopharmaceuticals, Society of Nuclear Medicine*, New York, p. 80, 1975.
Hnatowich, Layne, Childs, Lanteigne, Davis, Griffin, Doherty, *Science*, 220:613, 1983.
Khaw, Fallon, Strauss, Haber, *Science*, 209:295, 1980.
Kohler and Milstein, *Nature*, 256:495–497, 1975.
Krejcarek and Tucker, "Covalent attachment of chelating groups to macromolecules," *Biochem. Biophys. Res. Commun.*, 77:581–585, 1977.
Leung, Meares, Goodwin, *Int. J. Appl. Radiot. Isot.*, 29:687, 1978.
Meares, Goodwin, Leung, Girgis, Silvester, Nunn, Lavender, "Covalent attachment of metal chelates to proteins: The stability in vivo and in vitro of the conjugate of albumin with a chelate of $^{111}$indium," *Proc. Natl. Acad. Sci. U.S.A.*, 73:3803–3806, 1976.

Meares and Wensel, *Accts. Chem. Res.*, 17:202, 1984.

Sokolovsky, Riordan, Vallee, *Biochem. Biophys. Res. Commun.*, 27:20, 1967.

Sundberg, Meares, Goodwin, Diamanti, *Nature*, 250:587; *J. Med. Chem.*, 17:1304, 1974.

Yeh, Meares, Goodwin, *J Radioanal. Chem.*, 53:327, 1979.

Yeh, Sherman, Meares, "A new route to "bifunctional" chelating agents: conversion of amino adds to analogs of ethylenedinitrilotetraacetic acid," *Anal. Biochem.*, 100:152–159, 1979.

U.S. Pat. No. 5,362,754 by Raad et al.

U.S. patent application Ser. No. 08/317,309 by Raad et al.

What is claimed is:

1. A method of treating a systemic fungal infection comprising:
    (a) obtaining a therapeutically effective amount of a pharmaceutical composition comprising at least one chelator, at least one antifungal agent and a pharmaceutical excipient, diluent or adjuvant; and
    (b) administering said pharmaceutical composition to a patient having a fungal infection.

2. The method of claim 1, wherein said chelator in said pharmaceutical composition may be selected from the group of chelators consisting of EDTA free acid, EDTA 2Na, EDTA 3Na, EDTA 4Na, EDTA 2K, EDTA 2Li, EDTA 2NH$_4$, EDTA 3K, Ba(II)-EDTA, Ca(II)-EDTA, Co(II)-EDTA, Cu(II)-EDTA, Dy(III)-EDTA, Eu(III)-EDTA, Fe(III)-EDTA, In(III)-EDTA, La(III)-EDTA, Mg(II)-EDTA, Mn(II)-EDTA, Ni(II)-EDTA, Sm(III)-EDTA, Sr(II)-EDTA, Zn(II)-EDTA, CyDTA, DHEG, DTPA-OH, DTPA, EDDA, EDDP, EDDPO, EDTA-OH, EDTPO, EGTA, HBED, HDTA, HIDA, IDA, Methyl-EDTA, NTA, NTP, NTPO, O-Bistren, and TTHA.

3. The method of claim 2, wherein said chelator is EDTA.

4. The method of claim 1, wherein said antifungal agent may be selected from the group of antifungal agents consisting of Voriconazole, SCH 56592, ER30346, UK 9746, UK9751, T 8581, Flutrimazole, Cilofungin LY121019, Echinocandin, Pneumocandin, Pradimicins, Benanomicin, Ambisome, ABLC, Liposomal Amphotericin, ABCD, Liposomal Nystatin, Nikkomycin Z, Terbinafine, BF-796, MTCH 24, BTG-137586, RMP-7/Amphotericin B, Omoconazole, Amphotericin B, Nystatin, Natamycin, Clotrimazole, Miconazole, Ketoconazole, Terconazole, Econazole, Itraconazole, Fluconazole, Griseofulvin, and Flucytosine.

5. The method of claim 4, wherein said antifungal agent is Amphotericin B.

6. The method of claim 1, wherein said pharmaceutical composition comprises about 0.001 mg to about 1000 mg of chelator.

7. The method of claim 1, wherein said pharmaceutical composition comprises about 0.001 mg to about 1000 mg of antifungal agent.

8. The method of claim 1, wherein said pharmaceutical composition may be administered by injection, bronchoalveolar lavage, or by nasal drops, nasal spray, or nasal inhaler.

9. The method of claim 1, wherein said pharmaceutical composition may be administered by injection.

10. A method for treating a systemic fungal infection comprising administering to a patient a therapeutically effective amount of a pharmaceutical composition comprising at least one chelator, at least one antifungal agent and at least one monoclonal antibody, wherein said monoclonal antibody is operatively attached to said chelator.

* * * * *